(12) United States Patent  
Wallenstein et al.

(10) Patent No.: US 11,344,426 B2  
(45) Date of Patent: *May 31, 2022

(54) CORPECTOMY DEVICE AND METHODS OF USE THEREOF

(71) Applicant: K2M, Inc., Leesburg, VA (US)

(72) Inventors: Todd Wallenstein, Ashburn, VA (US); Clint Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 353 days.

This patent is subject to a terminal disclaimer.

(21) Appl. No.: 16/415,439

(22) Filed: May 17, 2019

(65) Prior Publication Data

US 2019/0269523 A1 Sep. 5, 2019

Related U.S. Application Data

(63) Continuation of application No. 15/268,948, filed on Sep. 19, 2016, now Pat. No. 10,327,908.

(Continued)

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/44* (2013.01); *A61F 2/4455* (2013.01);
(Continued)

(58) Field of Classification Search
CPC ......... A61F 2/44; A61F 2/4425; A61F 2/4455
See application file for complete search history.

(56) References Cited

U.S. PATENT DOCUMENTS

| 251,546 A | 12/1881 | Edison |
| 739,461 A | 9/1903 | Warren |

(Continued)

FOREIGN PATENT DOCUMENTS

| AU | 2015255166 A1 | 6/2016 |
| DE | 19804765 A1 | 8/1999 |

(Continued)

OTHER PUBLICATIONS

International Search Report and Written Opinion issued in corresponding PCT Application No. PCT/US2016/052433 dated Nov. 29, 2016.

(Continued)

*Primary Examiner* — Andrew Yang
(74) *Attorney, Agent, or Firm* — Lerner, David, Littenberg, Krumholz & Mentlik, LLP

(57) ABSTRACT

A spinal fixation device includes a housing defining a chamber and a longitudinal axis, and an end plate assembly operatively coupled with the housing. The end plate assembly includes a first end plate configured to engage a vertebral body and first and second support assemblies operatively coupled to the first end plate. The first support assembly is selectively movable between a first position in which the first end plate is spaced apart from the housing and a second position in which the first end plate is adjacent the housing. The second support assembly is transitionable between a first state in which the first end plate has a first angular orientation and a second state in which the first end plate has a second angular orientation.

21 Claims, 25 Drawing Sheets

Related U.S. Application Data

(60) Provisional application No. 62/220,274, filed on Sep. 18, 2015.

(52) U.S. Cl.
CPC ..... *A61F 2/4611* (2013.01); *A61F 2002/3055* (2013.01); *A61F 2002/30471* (2013.01); *A61F 2002/30507* (2013.01); *A61F 2002/30525* (2013.01); *A61F 2002/30538* (2013.01); *A61F 2002/30601* (2013.01); *A61F 2002/4615* (2013.01); *A61F 2002/4627* (2013.01); *A61F 2002/4629* (2013.01)

(56) References Cited

U.S. PATENT DOCUMENTS

| | | |
|---|---|---|
| 3,402,947 A | 9/1968 | Lewis |
| 3,588,023 A | 6/1971 | Cohen |
| 3,893,730 A | 7/1975 | Homier et al. |
| 4,387,926 A | 6/1983 | Van Eerden et al. |
| 4,554,914 A | 11/1985 | Kapp et al. |
| 4,938,319 A | 7/1990 | Ernst |
| 5,053,036 A | 10/1991 | Perren et al. |
| 5,108,066 A | 4/1992 | Lundstrom |
| 5,236,460 A | 8/1993 | Barber |
| 5,290,312 A | 3/1994 | Kojimoto et al. |
| 5,336,223 A | 8/1994 | Rogers |
| 5,360,430 A | 11/1994 | Lin |
| 5,458,641 A | 10/1995 | Ramirez Jimenez |
| 5,520,690 A | 5/1996 | Errico et al. |
| 5,547,308 A | 8/1996 | Wright |
| 5,571,190 A | 11/1996 | Ulrich et al. |
| 5,571,192 A | 11/1996 | Schonhoffer |
| 5,702,455 A | 12/1997 | Saggar |
| 5,723,013 A | 3/1998 | Jeanson et al. |
| 5,738,685 A | 4/1998 | Halm et al. |
| 5,776,198 A | 7/1998 | Rabbe et al. |
| 5,885,286 A | 3/1999 | Sherman et al. |
| 5,888,014 A | 3/1999 | Lung et al. |
| 5,901,798 A | 5/1999 | Herrera et al. |
| 5,904,683 A | 5/1999 | Pohndorf et al. |
| 5,980,522 A | 11/1999 | Koros et al. |
| 5,989,290 A | 11/1999 | Biedermann et al. |
| 6,074,391 A | 6/2000 | Metz-Stavenhagen et al. |
| 6,099,531 A | 8/2000 | Bonutti |
| 6,110,172 A | 8/2000 | Jackson |
| 6,132,434 A | 10/2000 | Sherman et al. |
| 6,176,881 B1 | 1/2001 | Schar et al. |
| 6,179,514 B1 | 1/2001 | Cheng |
| 6,183,517 B1 | 2/2001 | Suddaby |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,235,062 B1 | 5/2001 | Gramnas |
| 6,241,769 B1 | 6/2001 | Nicholson et al. |
| 6,254,602 B1 | 7/2001 | Justis |
| 6,273,888 B1 | 8/2001 | Justis |
| 6,296,642 B1 | 10/2001 | Morrison et al. |
| 6,296,665 B1 | 10/2001 | Strnad et al. |
| 6,302,888 B1 | 10/2001 | Mellinger et al. |
| 6,332,895 B1 | 12/2001 | Suddaby |
| 6,342,074 B1 | 1/2002 | Simpson |
| 6,364,880 B1 | 4/2002 | Michelson |
| 6,375,683 B1 | 4/2002 | Crozet et al. |
| 6,395,034 B1 | 5/2002 | Suddaby |
| 6,419,705 B1 | 7/2002 | Erickson |
| 6,423,063 B1 | 7/2002 | Bonutti |
| 6,440,170 B1 | 8/2002 | Jackson |
| 6,500,178 B2 | 12/2002 | Zucherman et al. |
| 6,524,341 B2 | 2/2003 | Lang et al. |
| 6,558,423 B1 | 5/2003 | Michelson |
| 6,562,074 B2 | 5/2003 | Gerbec et al. |
| 6,610,090 B1 | 8/2003 | Bohm et al. |
| 6,616,695 B1 | 9/2003 | Crozet et al. |
| 6,629,998 B1 | 10/2003 | Lin |
| 6,648,917 B2 | 11/2003 | Gerbec et al. |
| 6,660,038 B2 | 12/2003 | Boyer, II et al. |
| 6,663,060 B1 | 12/2003 | Gifford, Sr. |
| 6,716,214 B1 | 4/2004 | Jackson |
| 6,730,088 B2 | 5/2004 | Yeh |
| 6,752,832 B2 | 6/2004 | Neumann |
| 6,770,096 B2 | 8/2004 | Bolger et al. |
| 6,827,719 B2 | 12/2004 | Ralph et al. |
| 6,830,589 B2 | 12/2004 | Erickson |
| 6,834,840 B1 | 12/2004 | Metz et al. |
| 6,835,196 B2 | 12/2004 | Biedermann et al. |
| 6,837,889 B2 | 1/2005 | Shluzas |
| 6,843,791 B2 | 1/2005 | Serhan |
| 6,852,129 B2 | 2/2005 | Gerbec et al. |
| 6,863,673 B2 | 3/2005 | Gerbec et al. |
| 6,866,682 B1 | 3/2005 | An et al. |
| 6,869,112 B2 | 3/2005 | Guidetti |
| 6,869,433 B2 | 3/2005 | Glascott |
| 6,884,244 B1 | 4/2005 | Jackson |
| 6,893,443 B2 | 5/2005 | Frigg et al. |
| 6,896,677 B1 | 5/2005 | Lin et al. |
| 6,908,485 B2 | 6/2005 | Crozet et al. |
| 6,918,911 B2 | 7/2005 | Biedermann et al. |
| 6,945,975 B2 | 9/2005 | Dalton |
| 6,972,019 B2 | 12/2005 | Michelson |
| 6,984,234 B2 | 1/2006 | Bray |
| 7,001,385 B2 | 2/2006 | Bonutti |
| 7,025,787 B2 | 4/2006 | Bryan et al. |
| 7,033,394 B2 | 4/2006 | Michelson |
| 7,041,135 B2 | 5/2006 | Michelson |
| 7,052,499 B2 | 5/2006 | Steger et al. |
| 7,056,343 B2 | 6/2006 | Schafer et al. |
| 7,077,864 B2 | 7/2006 | Byrd, III et al. |
| 7,086,631 B2 | 8/2006 | Lee et al. |
| 7,087,057 B2 | 8/2006 | Konieczynski et al. |
| 7,094,257 B2 | 8/2006 | Mujwid et al. |
| 7,156,874 B2 | 1/2007 | Paponneau et al. |
| 7,175,624 B2 | 2/2007 | Konieczynski et al. |
| 7,229,443 B2 | 6/2007 | Eberlein et al. |
| 7,285,134 B2 | 10/2007 | Berry et al. |
| 7,318,825 B2 | 1/2008 | Butler et al. |
| 7,445,627 B2 | 11/2008 | Hawkes et al. |
| 7,527,640 B2 | 5/2009 | Ziolo et al. |
| 7,531,002 B2 | 5/2009 | Sutton et al. |
| 7,544,208 B1 | 6/2009 | Mueller et al. |
| 7,611,104 B1 | 11/2009 | Gifford, Sr. |
| 7,618,456 B2 | 11/2009 | Mathieu et al. |
| 7,651,517 B2 | 1/2010 | Konieczynski et al. |
| 7,691,147 B2 | 4/2010 | Gutlin et al. |
| 7,811,327 B2 * | 10/2010 | Hansell ............ A61F 2/442 623/17.15 |
| 7,862,616 B2 | 1/2011 | Lechmann et al. |
| 8,137,405 B2 | 3/2012 | Kostuik et al. |
| 8,353,961 B2 | 1/2013 | McClintock et al. |
| 8,377,101 B2 | 2/2013 | Barrus et al. |
| 8,439,977 B2 | 5/2013 | Kostuik et al. |
| 8,585,761 B2 | 11/2013 | Theofilos |
| 8,663,330 B2 | 3/2014 | McClintock et al. |
| 8,673,011 B2 | 3/2014 | Theofilos et al. |
| 8,801,791 B2 | 8/2014 | Soo et al. |
| 8,814,919 B2 | 8/2014 | Barrus et al. |
| 8,920,471 B2 | 12/2014 | Barrus et al. |
| 2001/0021851 A1 | 9/2001 | Eberlein et al. |
| 2002/0032443 A1 | 3/2002 | Sherman et al. |
| 2002/0128654 A1 | 9/2002 | Steger et al. |
| 2002/0161441 A1 | 10/2002 | Lang et al. |
| 2003/0130737 A1 | 7/2003 | McGahan et al. |
| 2003/0130739 A1 | 7/2003 | Gerbec et al. |
| 2003/0181980 A1 | 9/2003 | Berry et al. |
| 2004/0186569 A1 | 9/2004 | Berry |
| 2004/0247379 A1 | 12/2004 | Guidetti |
| 2005/0060034 A1 | 3/2005 | Berry et al. |
| 2005/0085910 A1 | 4/2005 | Sweeney |
| 2005/0209697 A1 | 9/2005 | Paponneau et al. |
| 2005/0218275 A1 | 10/2005 | Keating |
| 2005/0273173 A1 | 12/2005 | Gordon et al. |
| 2006/0041260 A1 | 2/2006 | Orbay |
| 2006/0074490 A1 | 4/2006 | Sweeney |
| 2006/0100710 A1 | 5/2006 | Gutlin et al. |

(56) References Cited

U.S. PATENT DOCUMENTS

| | | |
|---|---|---|
| 2006/0122701 A1 | 6/2006 | Kiester |
| 2006/0129244 A1 | 6/2006 | Ensign |
| 2006/0149251 A1 | 7/2006 | Ziolo et al. |
| 2006/0149385 A1 | 7/2006 | McKay |
| 2006/0173456 A1 | 8/2006 | Hawkes et al. |
| 2006/0200244 A1 | 9/2006 | Assaker |
| 2006/0212118 A1 | 9/2006 | Abernathie |
| 2006/0217715 A1 | 9/2006 | Serhan et al. |
| 2006/0241762 A1 | 10/2006 | Kraus |
| 2006/0241770 A1 | 10/2006 | Rhoda et al. |
| 2006/0271047 A1 | 11/2006 | Jackson |
| 2006/0276792 A1 | 12/2006 | Ensign et al. |
| 2007/0010887 A1 | 1/2007 | Williams et al. |
| 2007/0032871 A1 | 2/2007 | Michelson |
| 2007/0073298 A1 | 3/2007 | Beutter et al. |
| 2007/0093817 A1 | 4/2007 | Barrus et al. |
| 2007/0100340 A1 | 5/2007 | Lange et al. |
| 2007/0106231 A1 | 5/2007 | Snow et al. |
| 2007/0162126 A1 | 7/2007 | Karahalios et al. |
| 2007/0191954 A1 | 8/2007 | Hansell et al. |
| 2007/0219635 A1 | 9/2007 | Mathieu et al. |
| 2007/0250171 A1 | 10/2007 | Bonin |
| 2007/0255408 A1 | 11/2007 | Castleman et al. |
| 2007/0270964 A1 | 11/2007 | Strohkirch et al. |
| 2007/0270968 A1 | 11/2007 | Baynham et al. |
| 2007/0282441 A1 | 12/2007 | Stream et al. |
| 2008/0009946 A1 | 1/2008 | Douget et al. |
| 2008/0021555 A1 | 1/2008 | White et al. |
| 2008/0114467 A1 | 5/2008 | Capote et al. |
| 2008/0125864 A1 | 5/2008 | de Villiers et al. |
| 2008/0167720 A1 | 7/2008 | Melkent |
| 2008/0249624 A1 | 10/2008 | Josimovic-Alasevic et al. |
| 2008/0249625 A1 | 10/2008 | Waugh et al. |
| 2008/0288071 A1 | 11/2008 | Biyani et al. |
| 2009/0164019 A1 | 6/2009 | Hsu et al. |
| 2010/0005715 A1 | 1/2010 | Allsop et al. |
| 2010/0137919 A1 | 6/2010 | Wolter |
| 2010/0318092 A1 | 12/2010 | Butler et al. |
| 2011/0208248 A1 | 8/2011 | Barrus et al. |
| 2013/0274883 A1 | 10/2013 | McLuen et al. |
| 2014/0135931 A1 | 5/2014 | Popa et al. |
| 2014/0277503 A1 | 9/2014 | Mendel et al. |
| 2014/0277510 A1 | 9/2014 | Robinson et al. |
| 2015/0094814 A1 | 4/2015 | Emerick et al. |

FOREIGN PATENT DOCUMENTS

| | | |
|---|---|---|
| EP | 1878408 A1 | 1/2008 |
| EP | 3020375 A1 | 5/2016 |
| FR | 2902315 A1 | 12/2007 |
| SU | 01560184 A1 | 4/1990 |
| WO | 98/46173 | 10/1998 |
| WO | 03032812 A2 | 4/2003 |
| WO | 2008005627 A2 | 1/2008 |
| WO | 2009023016 A1 | 2/2009 |

OTHER PUBLICATIONS

Australian Search Report for Application No. 2016324333 dated Feb. 26, 2020, 1 page.
European Search Report for EP15194277 dated Feb. 23, 2016.
European Search Report for EP16847525 dated Apr. 2, 2019.

* cited by examiner

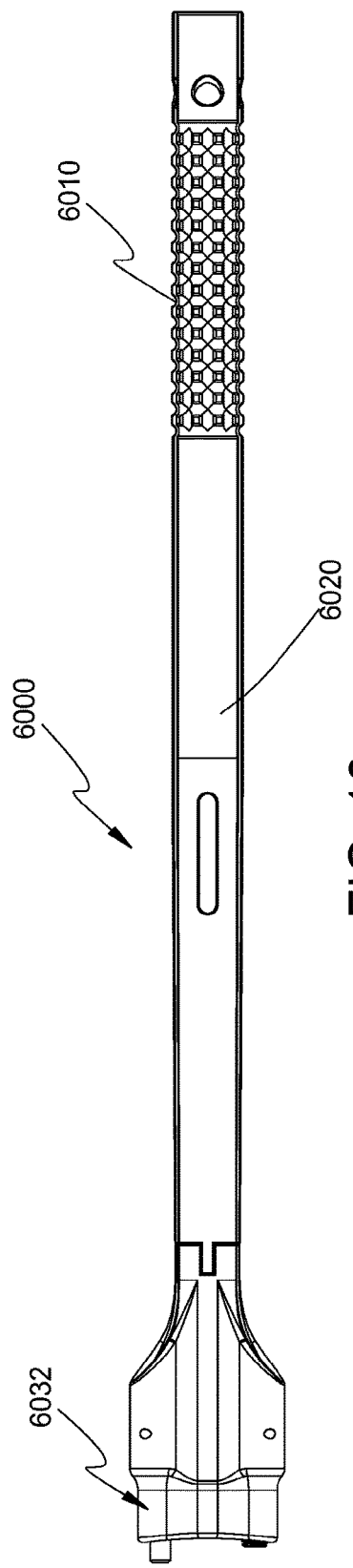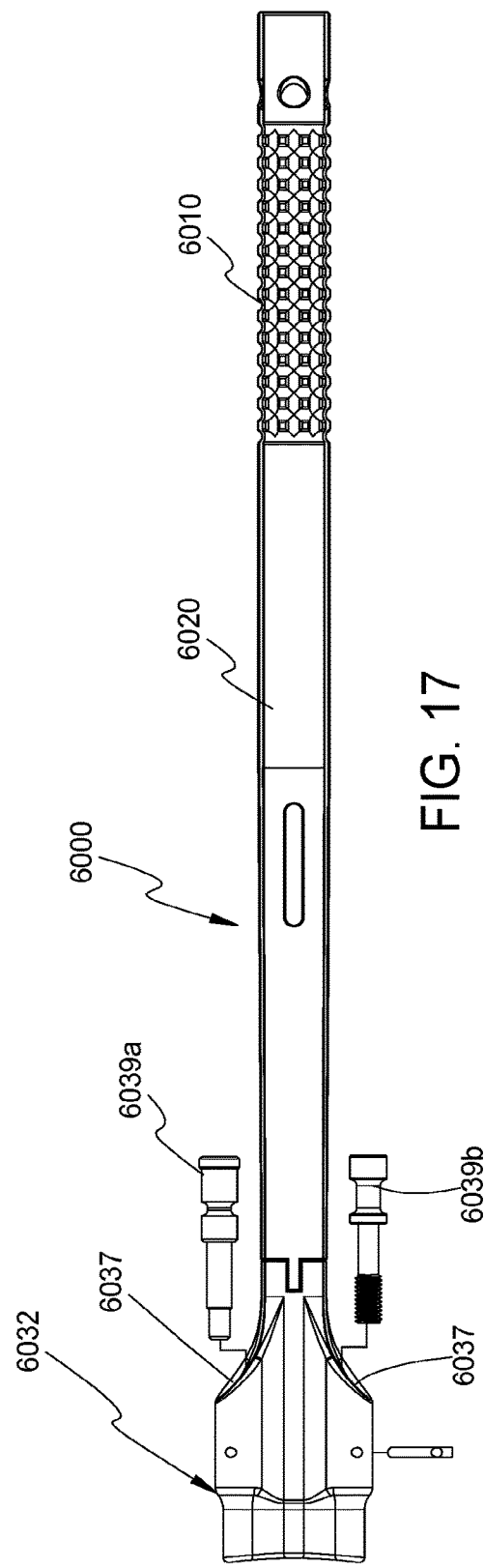

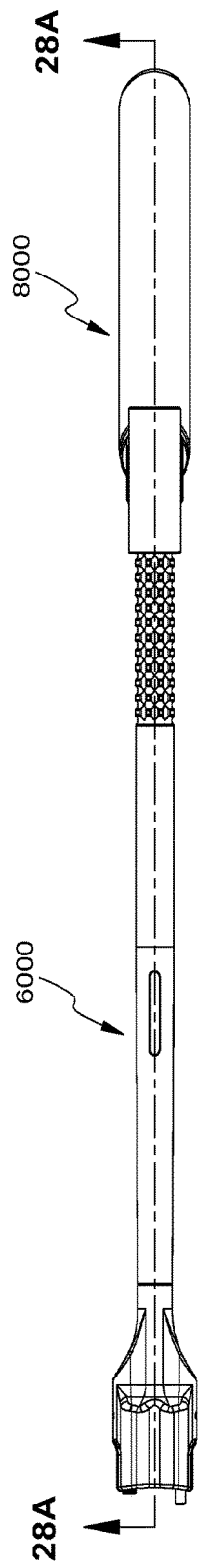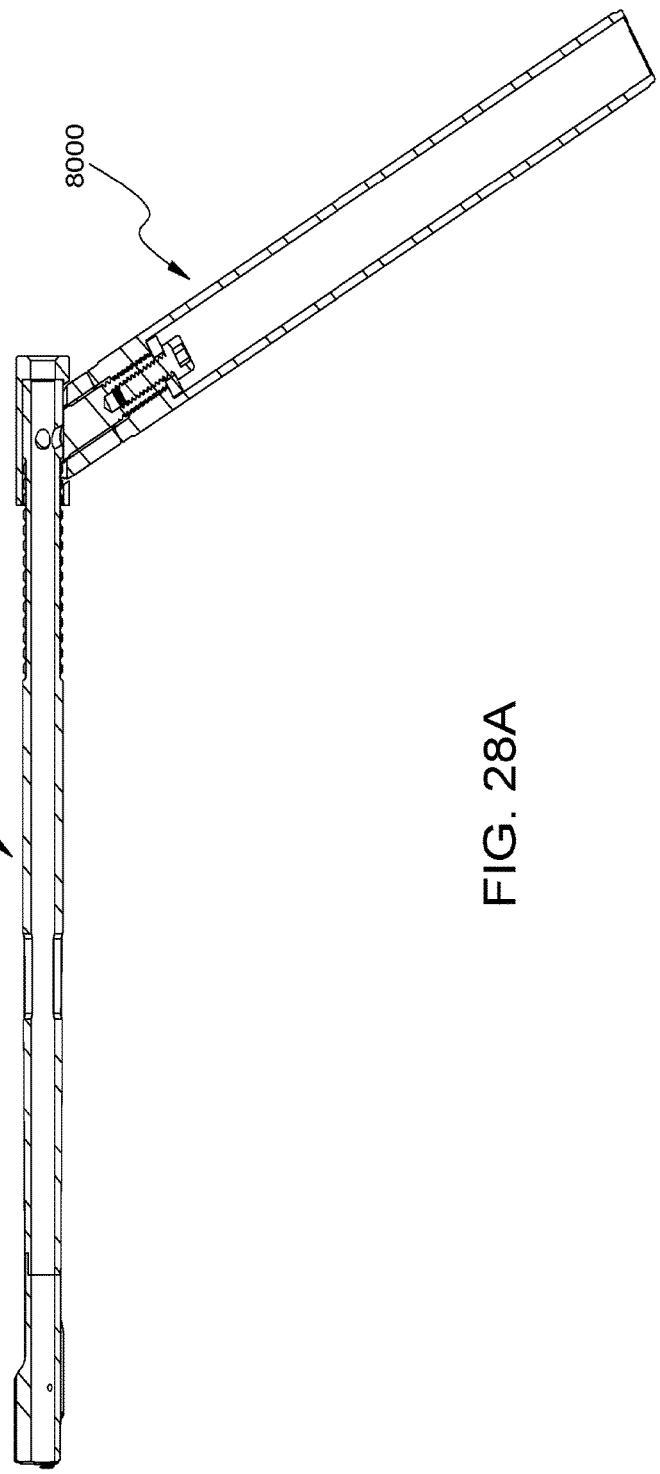
FIG. 28
FIG. 28A

CORPECTOMY DEVICE AND METHODS OF USE THEREOF

CROSS-REFERENCE TO RELATED APPLICATION

The present application is a continuation of U.S. patent application Ser. No. 15/268,948, filed on Sep. 19, 2016, which claims priority to, and the benefit of, U.S. Provisional Patent Application Ser. No. 62/220,274, filed on Sep. 18, 2015, the entire contents of which are incorporated by reference herein.

BACKGROUND

Technical Field

The present disclosure relates to an apparatus for treating spinal conditions, and more particularly, to an intervertebral implant.

Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located in each vertebra allows passage of the spinal cord. When the vertebrae are properly aligned, the spinal cord passes through without a problem. However, when the vertebrae are misaligned or a constriction is formed in the spinal canal, nerves of the spinal cord may get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to these methods and devices are nevertheless still possible. Reference may be made to U.S. Patent Publication No. 2014/0277503 filed on Mar. 14, 2014, entitled "Spinal Fixation Device," the entire content of which is incorporated herein by reference, for a detailed discussion of the construction and operation of a spinal fixation system and an instrumentation for use therewith.

Furthermore, intervertebral spacer implants used as a stand-alone device or provided in an assembly including a retention mechanism to help alleviate expulsion and movement of the implant when placed in the spine, are well known. Such implant assemblies are advantageous in providing an implant that is easier to insert in the spine. Intervertebral spacer implant assemblies which include a spacer and a plate, where the plate comprises a supplemental or alternative retention mechanism having one or more holes in the anterior end of the plate that are directed toward the superior, inferior or both end plates of adjacent vertebrae are also known in the art. Such implants are used to stabilize and immobilize the spinal segments in the treatment of single or multi-level degenerative disc disease, spinal stenosis, and failed previous fusions, as well as other spine conditions.

To meet the problem of preventing expulsion of the interbody device and for providing stability to the anatomy, a need exists for an spinal fixation device that can be secured to the spine and provide anterior column support and stabilization, while providing a maximum fusion area.

SUMMARY

In accordance with an embodiment of the present disclosure, there is provided a spinal fixation device including a housing defining a chamber and a longitudinal axis, and an end plate assembly operatively coupled with the housing. The end plate assembly includes a first end plate configured to engage a vertebral body and first and second support assemblies operatively coupled to the first end plate. The first support assembly is selectively movable between a first position in which the first end plate is spaced apart from the housing and a second position in which the first end plate is adjacent the housing. The second support assembly is transitionable between a first state in which the first end plate has a first angular orientation and a second state in which the first end plate has a second angular orientation. The first and second angular orientations are defined with respect to the longitudinal axis.

In an embodiment, the first support assembly may include a first support and a first rotatable member rotatably secured in the chamber of the housing. The first support may be rotatably coupled to the first rotatable member such that rotation of the first rotatable member causes axial displacement of the first support. The first support may include a protrusion portion pivotably coupled with the first end plate. The first support may define a slot along the longitudinal axis. The housing may include a pin configured to be received in the slot of the first support to facilitate axial movement of the first support.

In another embodiment, the housing may define a bore adjacent the first rotatable member.

In yet another embodiment, the housing may include an inner wall having a ledge to inhibit axial displacement of the first rotatable member.

In still yet another embodiment, the first rotatable member may include circumferentially arranged teeth.

In still yet another embodiment, the second support assembly may include a second support and a second rotatable member rotatably secured in a passage of the first support. The second support may be rotatably coupled to the second rotatable member such that rotation of the second rotatable member causes axial displacement of the second support. The second support may include a protrusion portion operatively coupled with the first end plate. The protrusion portion of the second support may define a bore configured to receive a pin. The first end plate may define a slot configured to receive the pin such that axial displacement of the second support enables selective transition of the first end plate from the first angular orientation to the second angular orientation.

In still yet another embodiment, the first support may define a locking bore adjacent the second rotatable member. The second rotatable member may include circumferentially arranged teeth.

In accordance with another embodiment of the present disclosure, there is provided a kit for spinal surgery. The kit includes a spinal fixation device and a surgical instrument. The spinal fixation device includes a housing defining a chamber and first and second end plate assemblies. The first end plate assembly is operatively coupled with the housing. The first end plate assembly includes a first end plate configured to engage a vertebral body and first and second support assemblies operatively coupled to the first end plate. The first support assembly is selectively movable between a first position in which the first end plate is spaced apart from the housing and a second position in which the first end plate is adjacent the housing. The second support assembly is movable between a first state in which the first end plate has a first angular orientation and a second state in which the first end plate has a second angular orientation. The second end plate assembly is interchangeable with the first end plate assembly. The second end plate assembly includes a second end plate having dimensions different from the first end plate, and third and fourth support assemblies. The third support assembly is selectively movable between a third position different from the first or second position of the first support assembly and a fourth position different from the first or second position of the first support assembly. The fourth support assembly is movable between a third state in which the second end plate has a third angular orientation different from the first or second angular orientation of the first end plate and a fourth state in which the second end plate defines a fourth angular orientation different from the first or second angular orientation of the first end plate. The surgical instrument includes an engaging portion configured to securely engage the housing of the spinal fixation device.

The surgical instrument may further includes a driver including an engaging portion having teeth configured to engage circumferentially arranged teeth of a first rotatable member of the first support assembly, such that rotation of the driver causes axial displacement of the first support of the first support assembly.

The first support may define a bore adjacent circumferentially arranged teeth of a second rotatable member. The bore of the first support may be dimensioned to receive the engaging portion of the driver of the surgical instrument to enable engagement of the teeth of the driver and the circumferentially arranged teeth of the second rotatable member, such that rotation of the driver causes axial displacement of the second support.

In accordance with another aspect of the present disclosure, there is provided a method of spinal surgery including positioning a spinal fixation device between adjacent vertebral bodies. The spinal fixation device includes a housing and an end plate assembly operatively coupled with the housing. The end plate assembly includes a first end plate configured to engage a vertebral body and first and second support assemblies operatively coupled to the first end plate. The method further includes adjusting a length of the spinal fixation device by transitioning the first support assembly from a first position in which the first end plate and the housing define a first distance to a second position in which the first end plate and the housing define a second distance different from the first distance; and varying an angular orientation of the first end plate with respect to a longitudinal axis defined by the spinal fixation device by transitioning the second support assembly from a first state in which the first end plate defines a first angular orientation to a second state in which the first end plate defines a second angular orientation.

In an embodiment, the method may further include securing the position of the first support assembly to maintain the length of the spinal fixation device. In addition, the method may further include securing the position of the second support assembly to maintain the angular orientation of the first end plate.

In another embodiment, inserting the spinal fixation device may include attaching a surgical insertion device to the housing.

In yet another embodiment, the method may further include distracting the adjacent vertebral bodies.

In yet another embodiment, adjusting the length of the spinal fixation device may include rotating a first rotatable member of the first support assembly to cause axial displacement of a first support coupled to the first end plate. Furthermore, varying the angular orientation of the first end plate may include rotating a second rotatable member of the second support assembly to cause axial displacement of a second support coupled to the first end plate.

BRIEF DESCRIPTION OF THE DRAWINGS

The above and other aspects and features of the present disclosure will become more apparent in light of the following detailed description when taken in conjunction with the accompanying drawings in which:

FIG. 16 is a top view of an insertion instrument for use with the spinal fixation device of FIG. 1;

FIG. 17 is a top view of the insertion instrument of FIG. 16 with securing members separated from the insertion instrument;

FIG. 28 is a top view of the insertion instrument and the extension member of FIG. 27;

FIG. 28A is a cross-sectional view of the insertion instrument and the extension member of FIG. 27 taken along section line 28A-28A of FIG. 28;

DETAILED DESCRIPTION OF THE EMBODIMENTS

Figure 1:
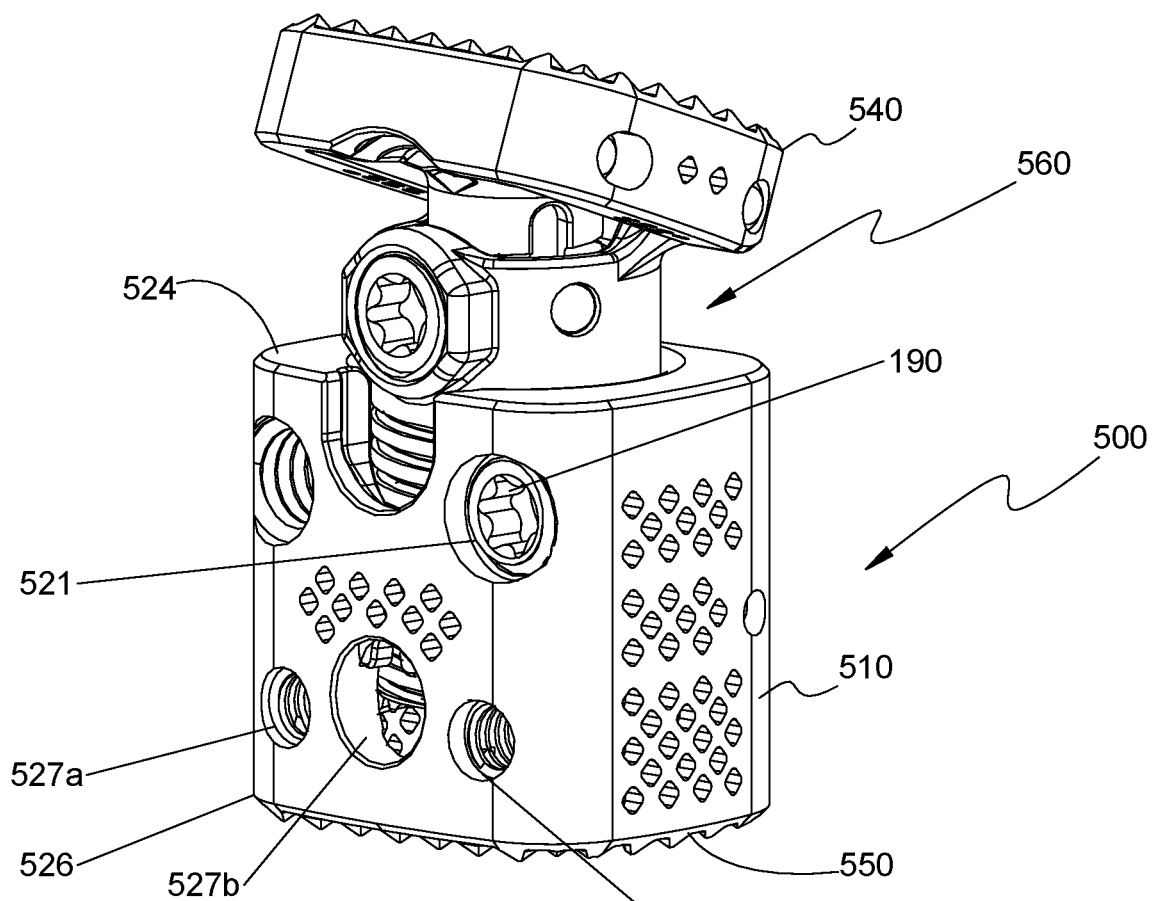
FIG. 1 is a perspective view of a spinal fixation device in accordance with an embodiment of the present disclosure.
Figure 2:
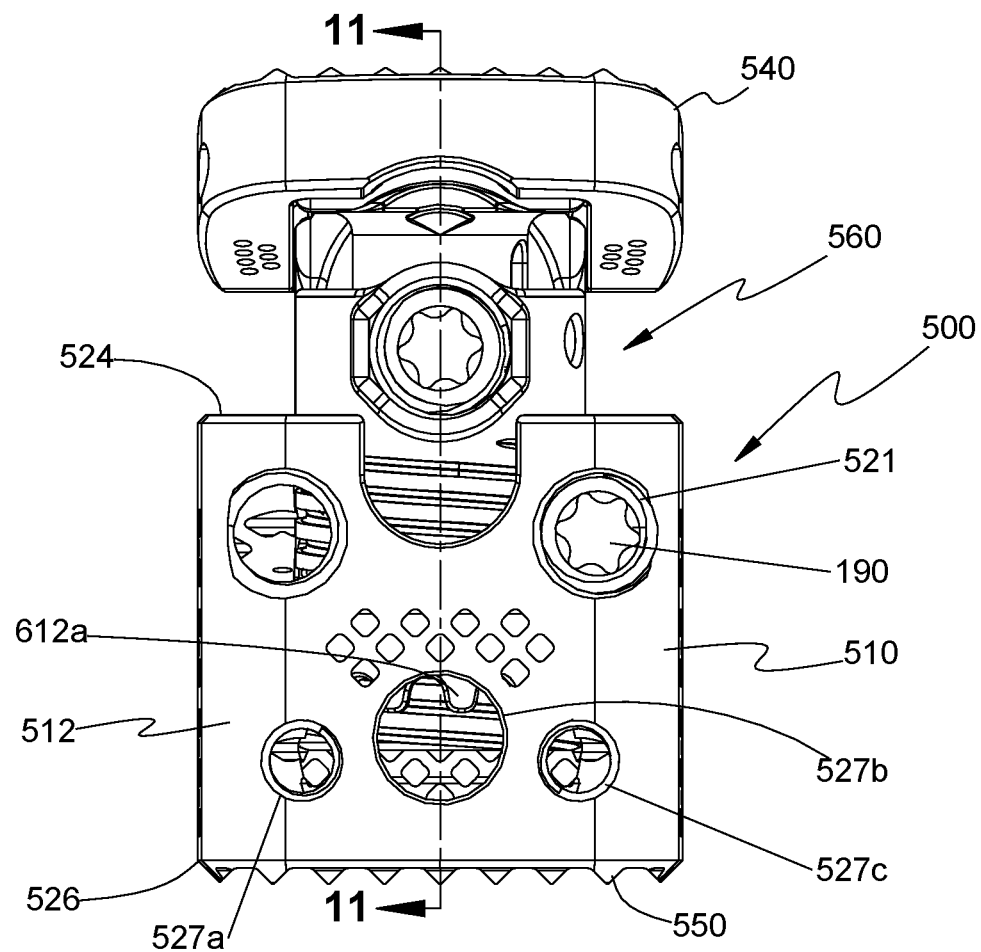
FIG. 2 is a front view of the spinal fixation device of FIG. 1.
Figure 3:
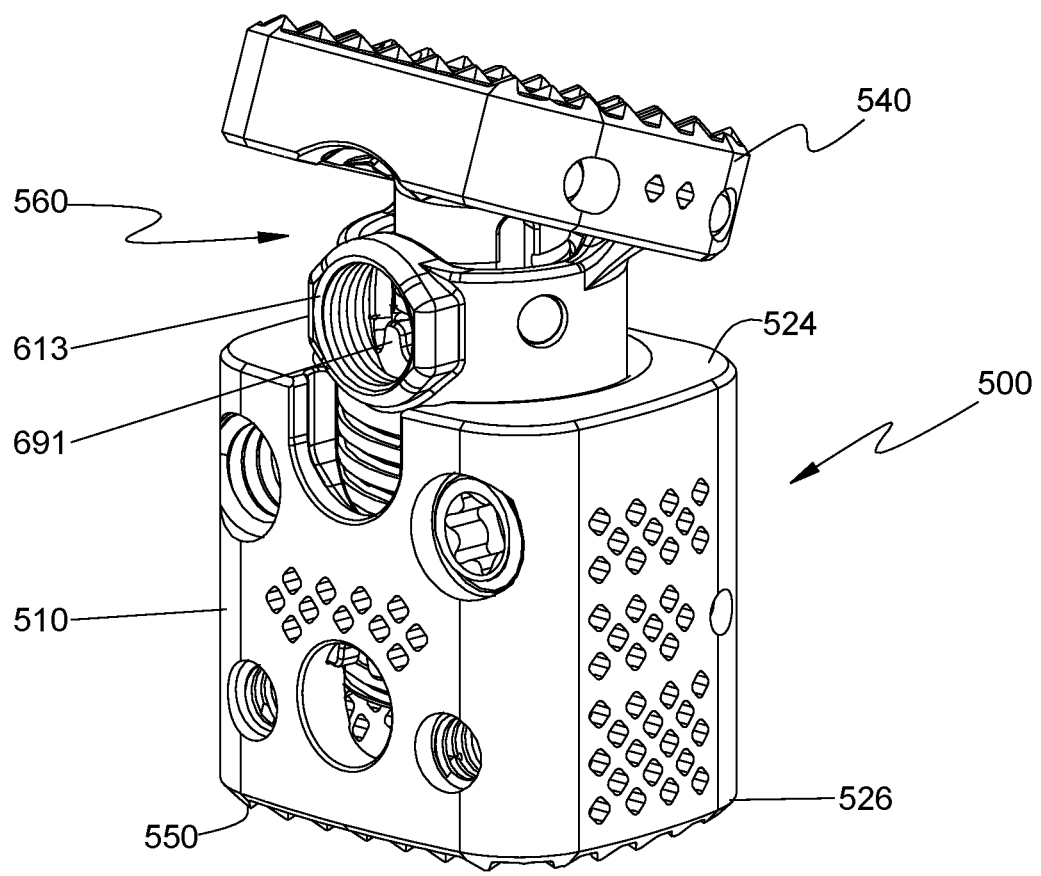
FIGS. 3 and 4 are perspective views of the spinal fixation device of FIG. 1 with a locking screw removed.
Figure 4:
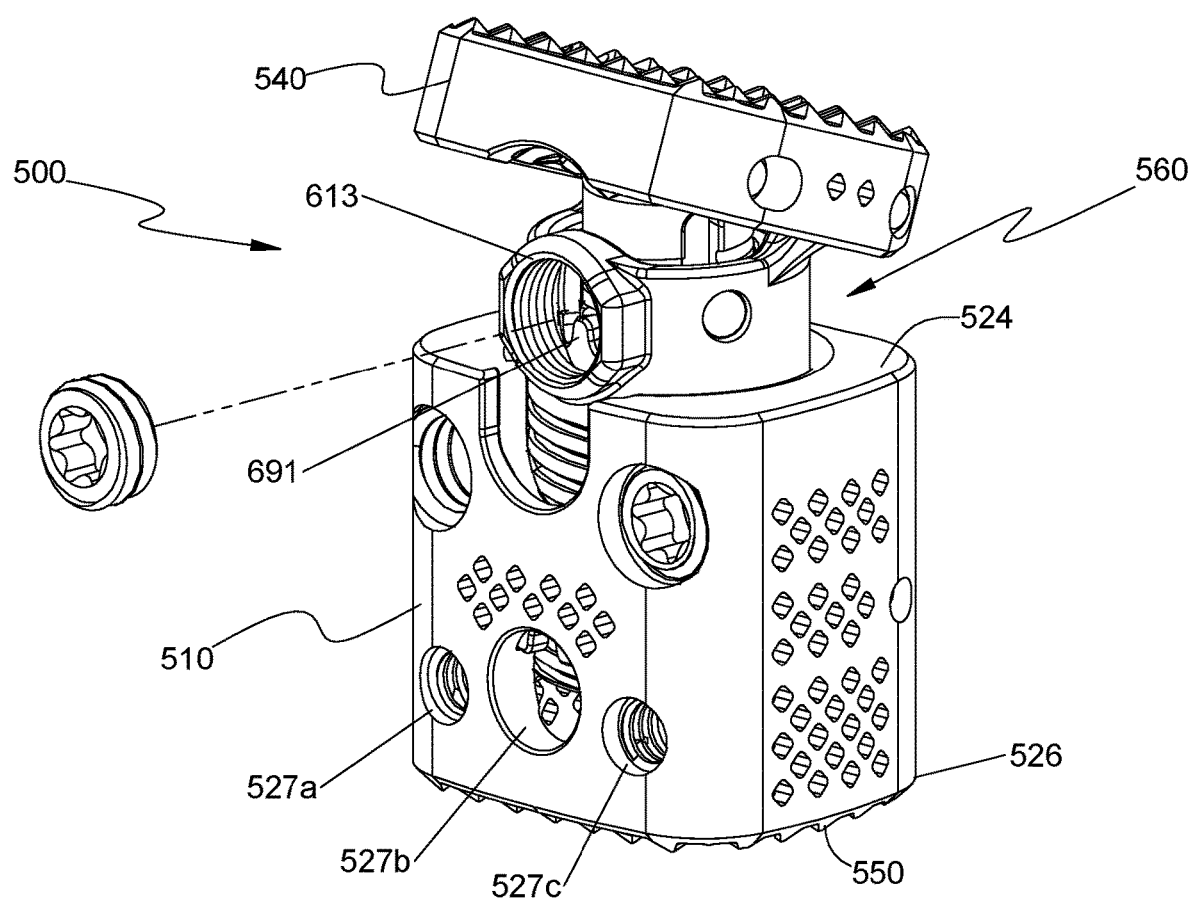

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

With reference to FIGS. 1-4, an embodiment of the present disclosure is shown generally as a spinal fixation device 500 configured and adapted to be positioned between vertebral bodies to support vertebral bodies and to promote spinal fusion. By way of example, spinal fixation device 500 may be inserted into the patient laterally, posteriorly, anteriorly, or obliquely. Additionally, spinal fixation device 500 may be inserted into the patient through procedures such as, e.g., posterior lumbar interbody fusion (PLIF), transforaminal lumbar interbody fusion (TLIF), lateral lumbar interbody fusion (LLIF), oblique lumbar interbody fusion (OLIF), or lateral extracavitary (LECA) procedures.

Figure 5:
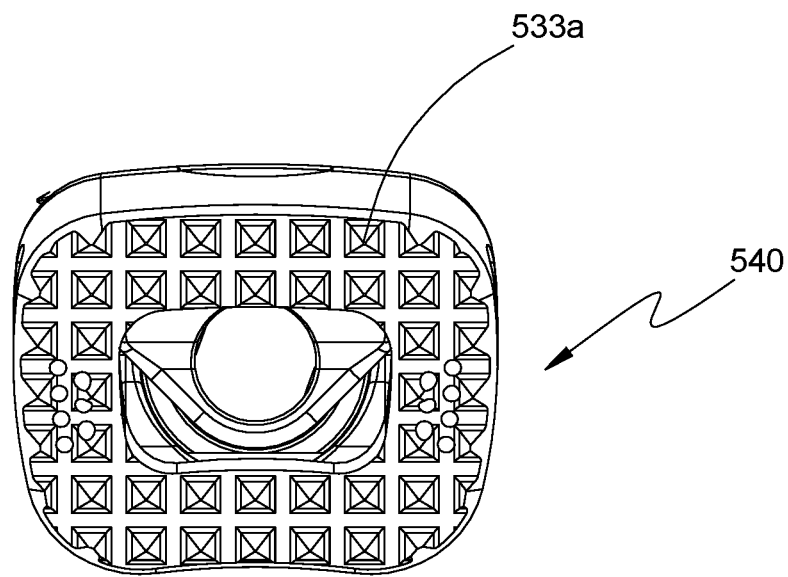
FIG. 5 is a top view of a first end plate of the spinal fixation device of FIG. 1.
Figure 6:
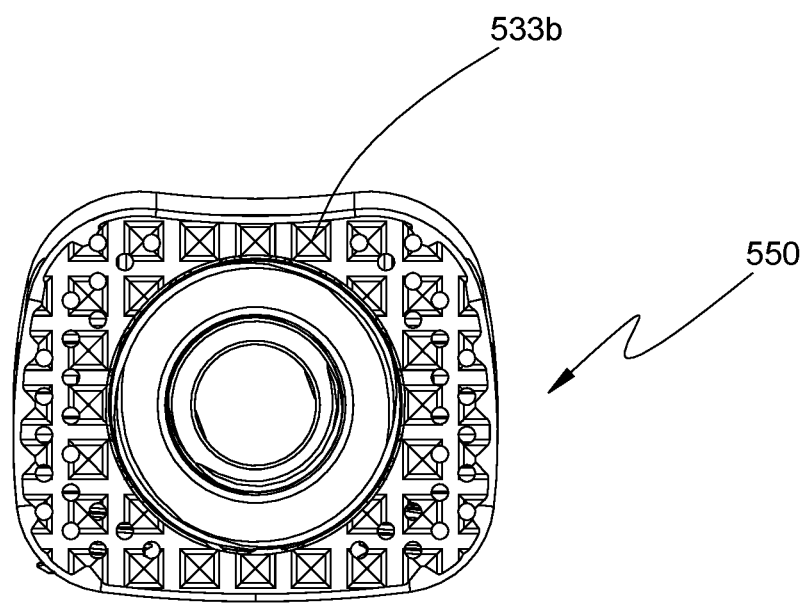
FIG. 6 is a bottom view of a second end plate of the spinal fixation device of FIG. 1.

With reference to FIGS. 1-4 and 7, spinal fixation device 500 includes a housing 510 and an end plate assembly 560 interchangeably coupled with housing 510. End plate assembly 560 includes a first end plate 540 and first and second support assemblies 660, 680 operatively supporting first end plate 540. Housing 510 includes a second end plate 550. First and second end plates 540, 550 are configured to engage end plates of adjacent vertebral bodies. In particular, first and second end plates 540, 550 are configured to engage, e.g., endplates of superior and inferior vertebral bodies, respectively. With brief reference to FIGS. 5 and 6, each of first and second end plates 540, 550 may include a plurality of pyramidal shaped spikes 533a, 533b (i.e., tetrahedrons) to aid in securing spinal fixation device 500 to the adjacent vertebral bodies for enhanced gripping of the vertebral bodies and minimizing movement of spinal fixation device 500 relative to the vertebral bodies. However, it is also contemplated that each of first and second end plates 540, 550 may include ridges or similar projections to aid in securing spinal fixation device 500 to the vertebral bodies.

End plate assembly 560 may be configured as a modular assembly that is interchangeably mounted in housing 510. For example, a plurality of end plate assemblies 560 may be provided with varying parameters such as, e.g., footprint and lordosis, such that the clinician may selectively attach a desired end plate assembly 560 to housing 510 to meet the needs of each patient or surgical procedure being performed. In this manner, end plate assembly 560 may be tailored to achieve a desired lordosis of first end plate 540 and a desired axial spacing between housing 510 and first end plate 540, as will be discussed hereinbelow. It is also contemplated that the desired axial spacing between first and second end plates 540, 550 may be tailored by selecting a desired length of housing 510 and/or end plate assembly 560.

Spinal fixation device 500 may be made of titanium, titanium alloy, stainless steel, allograft bone, autologous bone graft, polyetheretherketone (PEEK), cobalt chrome, polymeric materials, a combination thereof, or any other suitable biocompatible material. In particular, spinal fixation device 500 may be formed of bone, or an artificial material other than bone which may be harder or stronger than bone, such as, e.g., ceramic materials. For example, various parts of spinal fixation device 500 such as, e.g., first and second end plates 540, 550, may be formed of titanium by 3D printing. Housing 510 may include a bone growth promoting material such as, e.g., bone morphogenic protein and hydroxyapatite. Housing 510 may define a cavity 551 to accommodate bone graft material therein. It is envisioned that bone support matrix can be placed within cavity 551 of housing 510. As used herein, a "bone support matrix" is a material that facilitates osteogenesis. Suitable bone support matrices can be resorbable or nonresorbable and osteoconductive or osteoinductive. Non-limiting examples of suitable bone support matrices include synthetic materials, bone morphogenic proteins (BMPs), and heterologous, homologous, or autologous bone and derivatives thereof. The bone support matrix may be radiolucent on x-rays.

Figure 7:
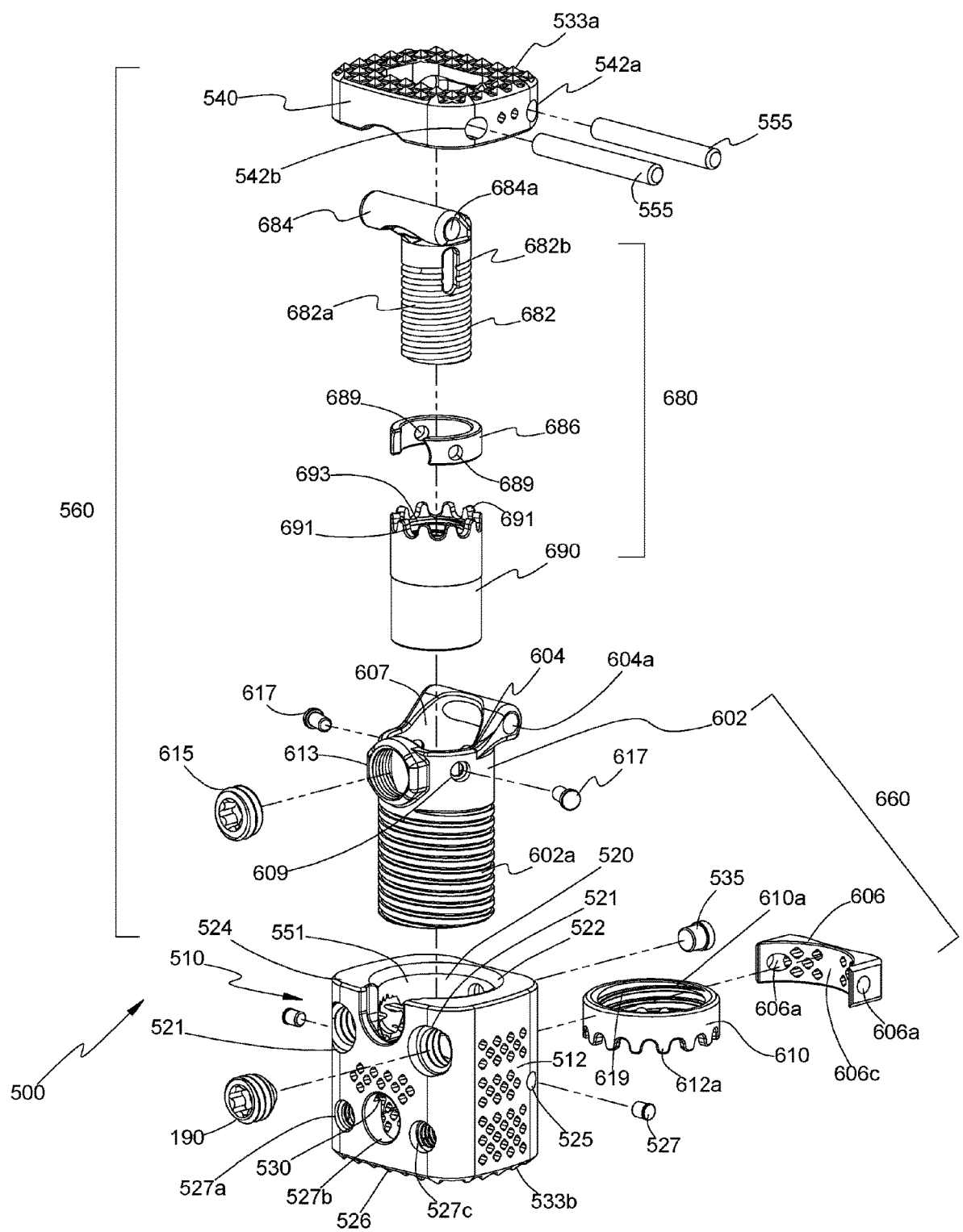
FIG. 7 is an exploded, front perspective view of the spinal fixation device of FIG. 1 with parts separated.
Figure 8:
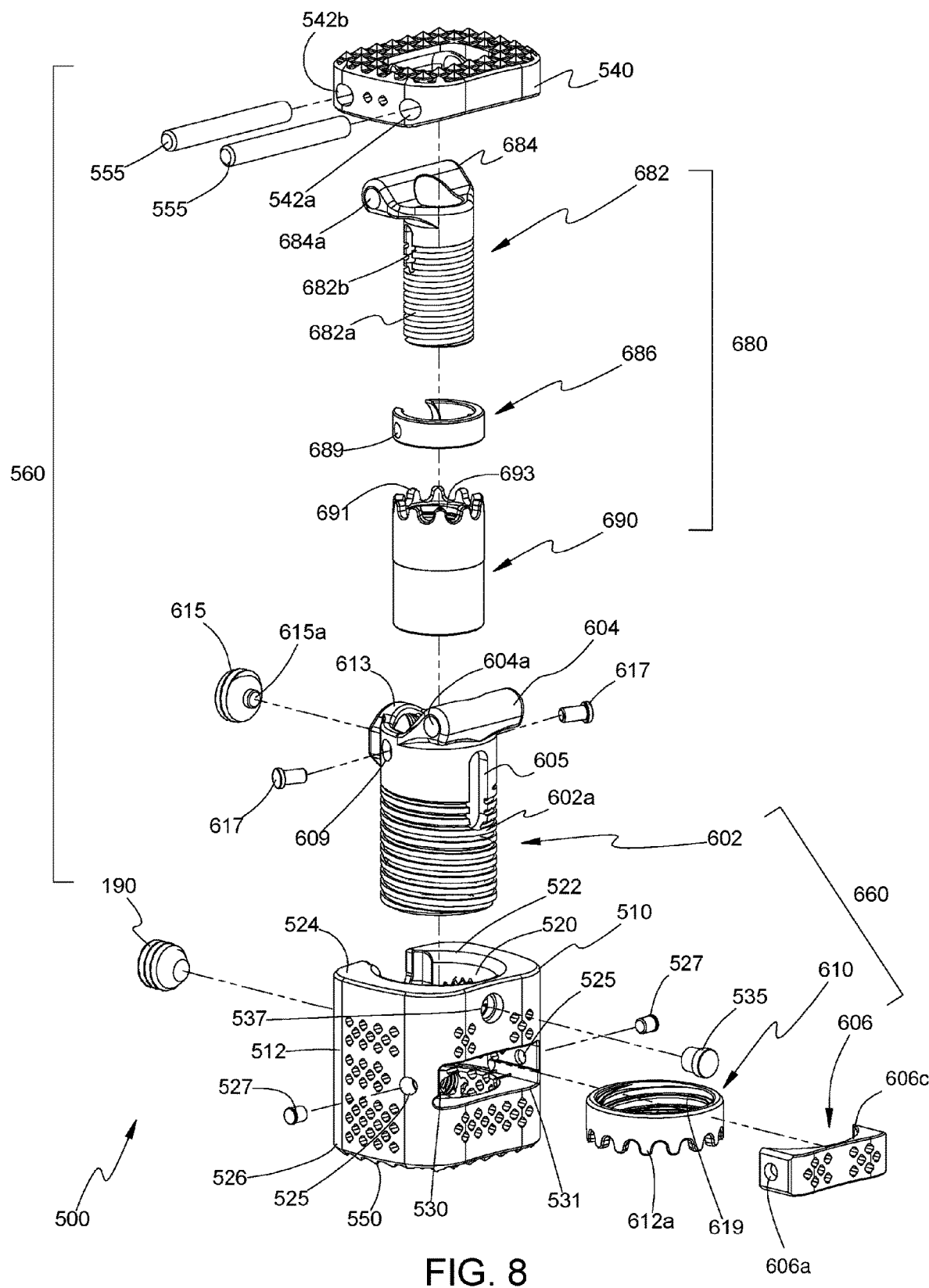
FIG. 8 is an exploded, rear perspective view of the spinal fixation device of FIG. 1 with parts separated.
Figure 18:
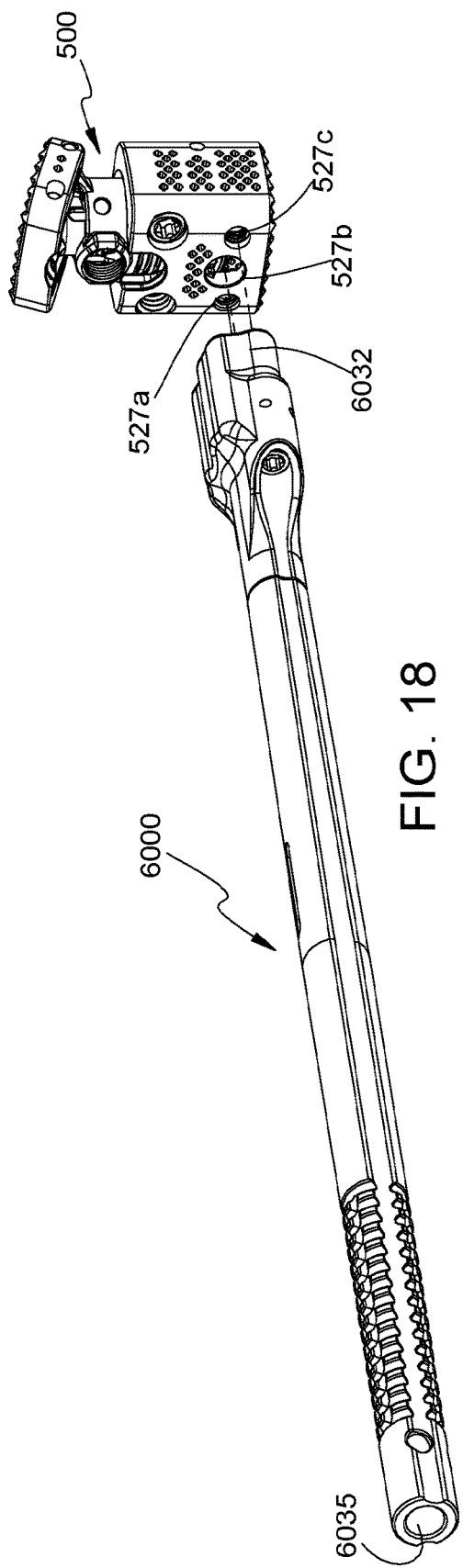
FIGS. 18 and 19 are perspective views of the insertion instrument illustrating use with the spinal fixation device of FIG. 1.

With reference to FIGS. 7 and 8, housing 510 includes first and second ends 524, 526 and an outer wall 512 extending between first and second ends 524, 526. Outer wall 512 defines bores 527a, 527b, 527c dimensioned to operatively engage insertion instrument 6000 (FIGS. 18 and 19), as will be discussed hereinbelow. For example, bores 527a, 527b, 527c may be defined in anterior or anterolateral portions of housing 510. Outer wall 512 may further define a slot 531 (FIG. 8) and bores 525 dimensioned to receive pins 527 to operatively secure first support assembly 660 in housing 510, as will be discussed hereinbelow. Outer wall 512 further defines a bore 537 dimensioned to receive a pin 535 that slides along a slot 605 defined in first support 602 in order to guide and facilitate axial movement of first support 602 within housing 510. The length of slot 605 may define a range of axial displacement of first and second support assemblies 660, 680. Thus, the length of slot 605 may be tailored to meet the needs of each surgical procedure. For example, slot 531 and bores 525, 537 may be defined in posterior or posterolateral portions of housing 510.

With continued reference to FIGS. 7 and 8, first end 524 of housing 510 defines an aperture 522 and second end 526 of housing 510 includes second end plate 550, e.g., integrally formed, with housing 510. Housing 510 defines a chamber 520 configured to receive at least a portion of end plate assembly 560 through aperture 522. End plate assembly 560 is selectively positionable within chamber 520. End plate assembly 560 includes a first support assembly 660 releasably supported on a shoulder 530 (FIG. 11) of housing 510 and a second support assembly 680 operatively coupled with first support assembly 660.

First support assembly 660 includes a first support 602, a spacer 606, and a first rotatable member 610 rotatably supported on shoulder 530 (FIG. 11) of housing 510. First support 602 includes a threaded portion 602a threadably coupled to first rotatable member 610, and a protrusion portion 604 (FIG. 12) defining a bore 604a therethrough. Bore 604a is dimensioned to receive a pin 555 such that protrusion portion 604 is, e.g., pivotably, coupled to first end plate 540. First support 602 defines a passage 607 dimensioned to receive at least a portion of second support assembly 680. First support 602 further defines bores 609 dimensioned to receive pins 617 to operatively secure second support assembly 680 to first support 602. First support 602 further defines a locking bore 613 providing access to second rotatable member 690. Locking bore 613 is also dimensioned to receive a screw 615 to inhibit relative movement between second support assembly 680 and first support 602.

First rotatable member 610 is positioned on shoulder 530 (FIG. 11) of housing 510 through slot 531 (FIG. 8) defined in, e.g., posterior or posterolateral portions, of housing 510. Spacer 606 is placed in slot 531 to enclose and rotatably secure first rotatable member 610 within chamber 520 of housing 510. Spacer 606 may act as a barrier to prevent any debris, tissue, or bone from entering any gaps that may be present between housing 510 and first rotatable member 610. Further, spacer 606 may also inhibit debris from depositing in teeth 612a of first rotatable member 610.

Spacer 606 includes an arcuate surface 606c configured to enable rotation of first rotatable member 610. Spacer 606 defines opposing bores 606a configured to be aligned with bores 525 (FIG. 8) defined in housing 510 to receive respective pins 527 therein to secure spacer 606 with housing 510. Housing 510 further includes a ledge 571 (FIG. 11) such that when first rotatable member 610 is disposed on shoulder 530 of housing 510, ledge 571 and shoulder 530 inhibit axial displacement of first rotatable member 610 within chamber 520 of housing 510. Under such a configuration, rotation of first rotatable member 610 causes axial displacement of first support 602 threadably coupled with inner threads 619 (FIG. 7) of first rotatable member 610. In this manner, the distance between first end plate 540 and housing 510 may be selectively adjusted.

For example, a length of spinal fixation device 500 can range from about 18 mm to about 32 mm. The length of spinal fixation device 500 may be based in part on the initial length of the device. For example, the length of the spinal fixation device 500 may be increased by an additional 4 mm. It is envisioned that the length of spinal fixation device 500 may be increased in any increment from about 0 mm to about 16 mm.

Figure 9:
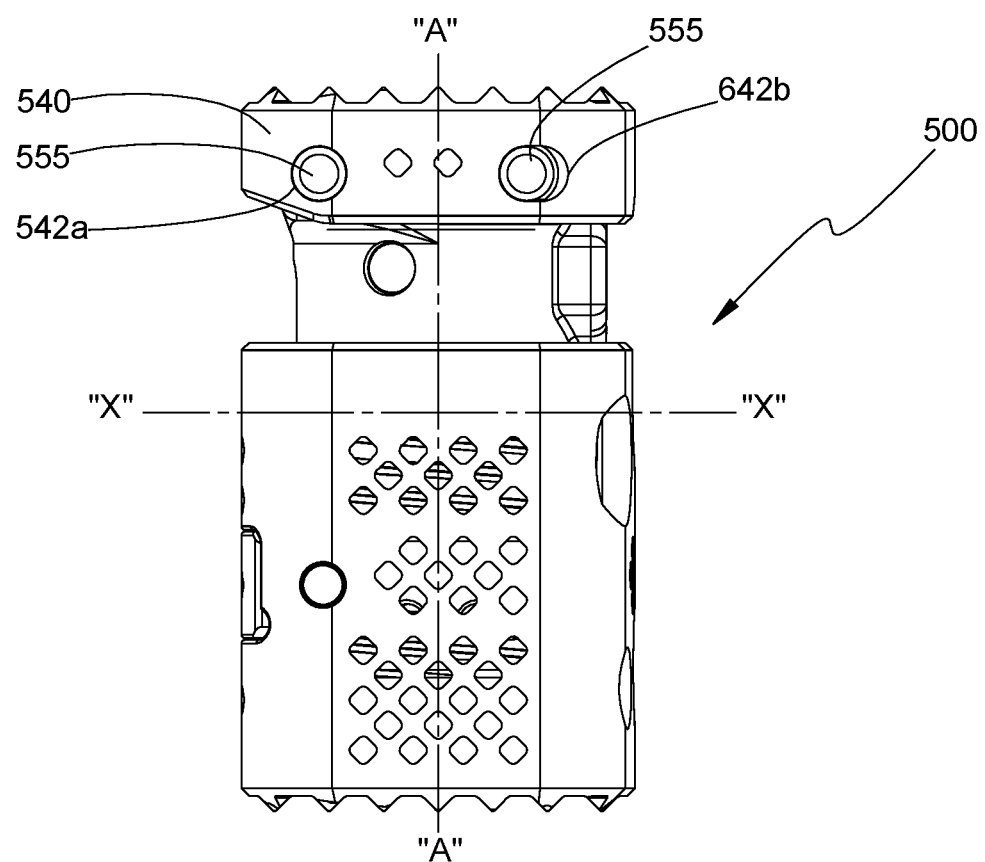
FIG. 9 is a side view of the spinal fixation device of FIG. 1.

With continued reference to FIGS. 7 and 8, second support assembly 680 is operatively coupled to first end plate 540 to selectively adjust the angular orientation of first end plate 540 with respect to longitudinal axis "A-A" (FIG. 9). With brief reference to FIGS. 12-15, second support assembly 680 includes a second support 682 translatably disposed within passage 607 of first support 602, a second spacer 686, and a second rotatable member 690 rotatably supported within passage 607 of first support 602. Second support 682 includes a threaded portion 682a threadably coupled to second rotatable member 690, and a protrusion portion 684 defining a bore 684a therethrough. Bore 684a is dimensioned to receive pin 555 (FIG. 8) such that protrusion portion 684 is coupled to first end plate 540. Second support 682 further defines slots 682b dimensioned to receive respective pins 617 extending through bores 609 of first support 602 to slidably secure second support 682 with first support 602.

With continued reference to FIGS. 7 and 8, second spacer 686 defines bores 689 aligned with respective slots 682b of second support 682 and bores 609 of first support 602 such that pins 617 are received through respective bores 609 of first support 602, bores 689 of second spacer 686, and slots 682b of second support 682. In this manner, second spacer 686 is secured with first support 602 while enabling axial displacement of second support 682 relative to first support 602. Second spacer 686 may act as a barrier to prevent any debris, tissue, or bone from entering any gaps that may be present between the first support 602 and second rotatable member 690. Furthermore, spacer 686 may also inhibit debris from depositing in teeth 691 of second rotatable member 690.

Figure 11:
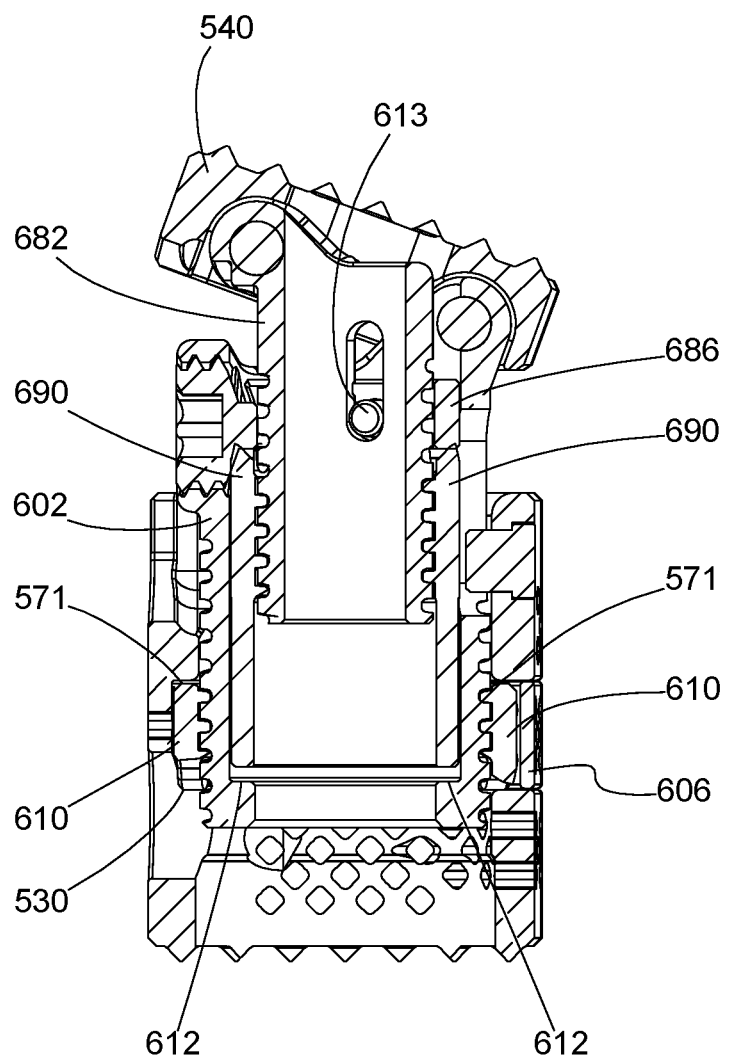
FIG. 11 is a side cross-sectional view of the spinal fixation device of FIG. 2 taken along section line 11-11 of FIG. 2.
Figure 12:
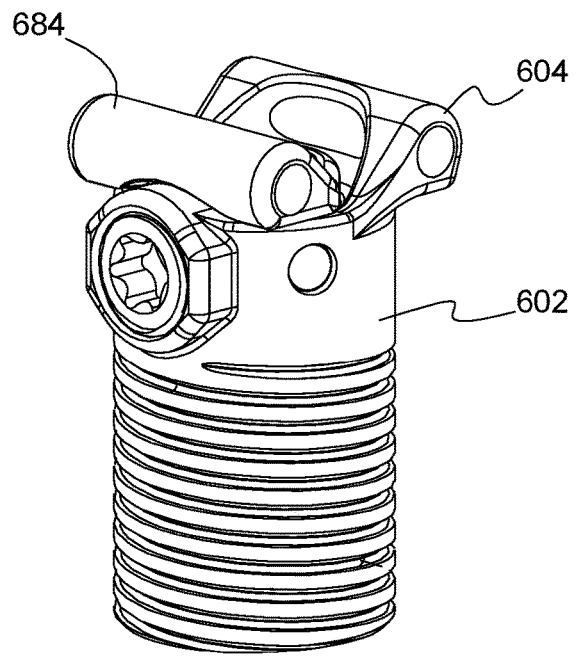
FIG. 12 is a perspective view of a partial end plate assembly of the spinal fixation device of FIG. 1.
Figure 13:
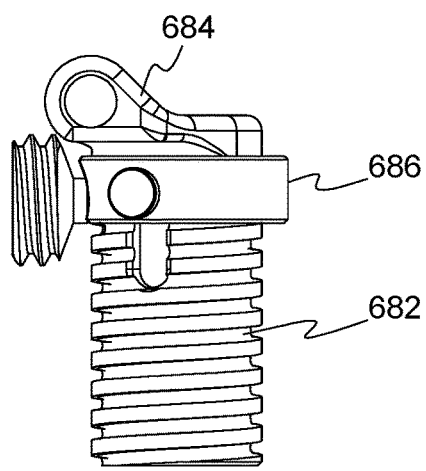
FIG. 13 is a side view of the second support assembly of FIG. 12.
Figure 14:
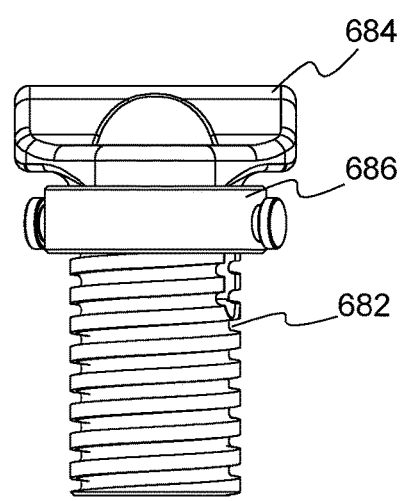
FIG. 14 is a rear view of the second support assembly of FIG. 12.
Figure 15:
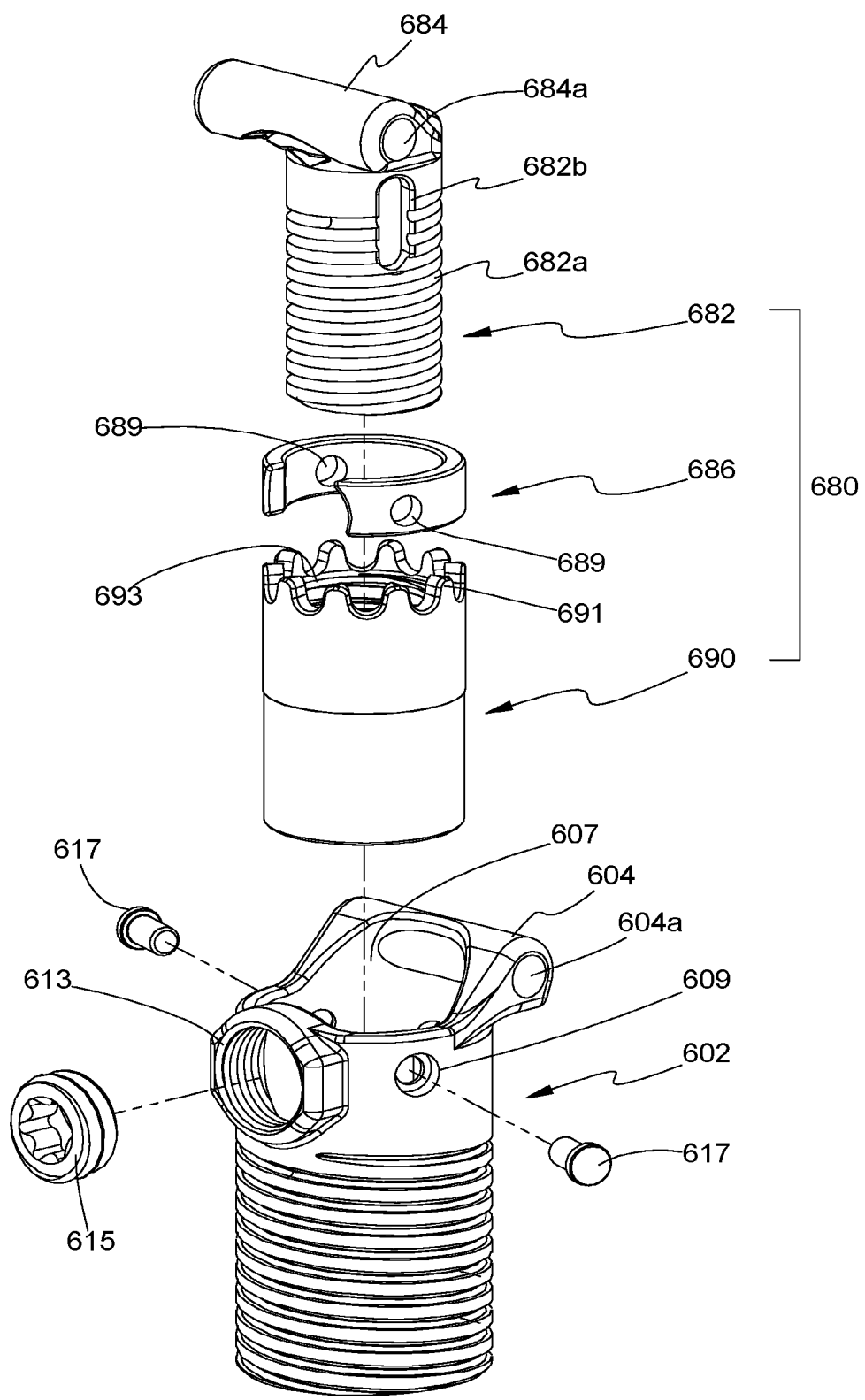
FIG. 15 is an exploded, perspective view of the partial end plate assembly of FIG. 12 with parts separated.

With brief reference to FIGS. 7, 8, and 11, at least a portion of second rotatable member 690 of second support assembly 680 is rotatably disposed within passage 607 of first support 602. In particular, second rotatable member 690 is disposed on a shoulder 612 of first support 602. Under such a configuration, shoulder 612 of first support 602 and second spacer 686 inhibit axial displacement of second rotatable member 690 while enabling rotation of second rotatable member 690. Second rotatable member 690 includes an inner wall 693 threadably coupled with threaded portion 682a of second support 682. In this manner, rotation of second rotatable member 690 causes axial displacement of second support 682 relative to first support 602 and housing 510. Bore 684a of protrusion portion 684 of second support 682 is aligned with slot 542b of first end plate 540 such that pin 555 is received in slot 542b of first end plate 540 and bore 648a of protrusion portion 684 of second support 682. Under such a configuration, axial displacement of second support 682 causes angular displacement of first end plate 540. In particular, first end plate 540 may pivot about pin 555 disposed within bore 542a of first end plate 540. Slot 542b has a larger dimension than pin 555 to facilitate pivoting of first end plate 540 about pin 555 in bore 542a. While second support assembly 680 is shown to selectively adjust the angular orientation of first end plate 540 with respect to longitudinal axis "A-A" (FIG. 9), it is also envisioned that second support assembly 680 may be operatively coupled to first end plate 540 to further adjust the distance between first end plate 540 and housing 510.

Housing 510 defines an axis "X-X" (FIG. 9) orthogonal to a longitudinal axis "A-A" (FIG. 9) defined by outer housing 510. For example, first end plate 540 may define a 0° angle with respect to axis "X-X" (i.e., a 90° angle with respect to axis "A-A"). Angular orientation of first end plate 540 may be selectively adjustable to better align first end plate 540 with an adjacent vertebral body to more accurately align spinal fixation device 500 with the adjacent vertebral body. First end plate 540 may be selectively adjustable in a range from about 0° to about 45° with respect to axis "X-X" (i.e., from about 90° to about 135° with respect to axis "A-A").

Figure 19:
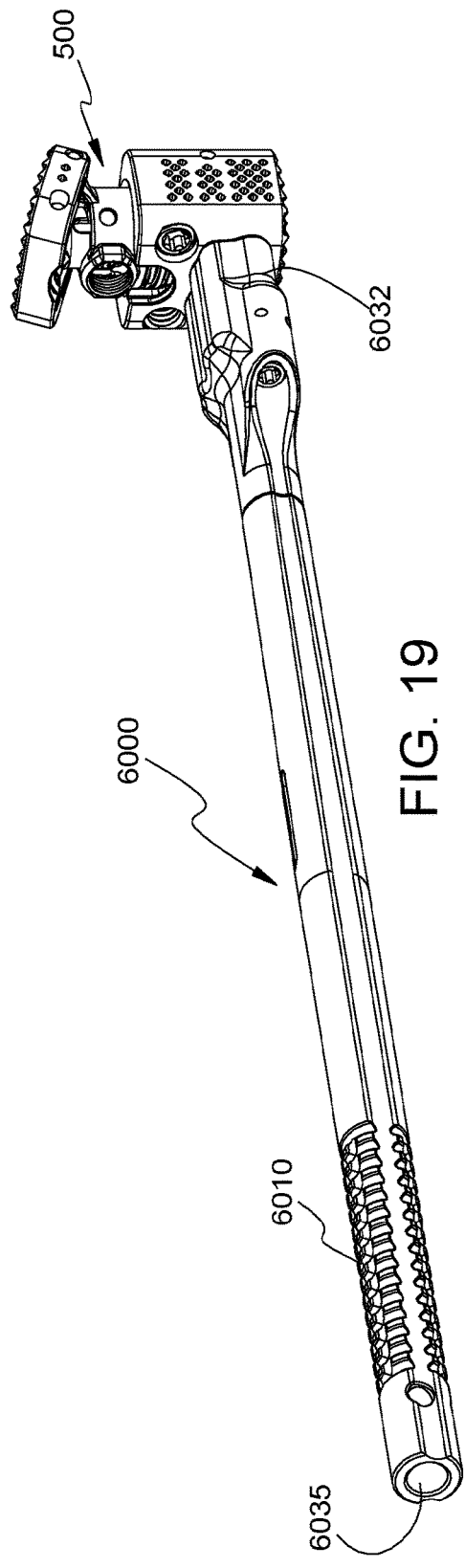
Figure 20:
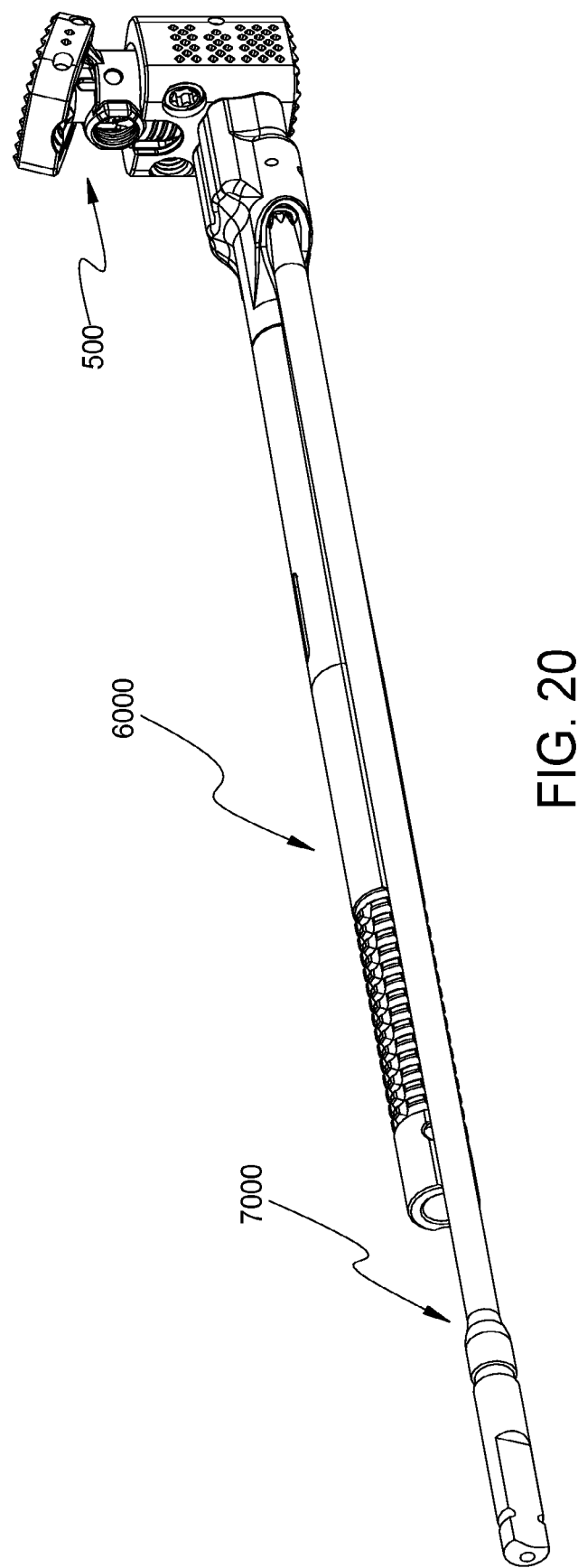
FIGS. 20-23 are perspective views of the insertion instrument of FIG. 16 and an adjusting driver illustrating use with the spinal fixation device of FIG. 1.
Figure 21:
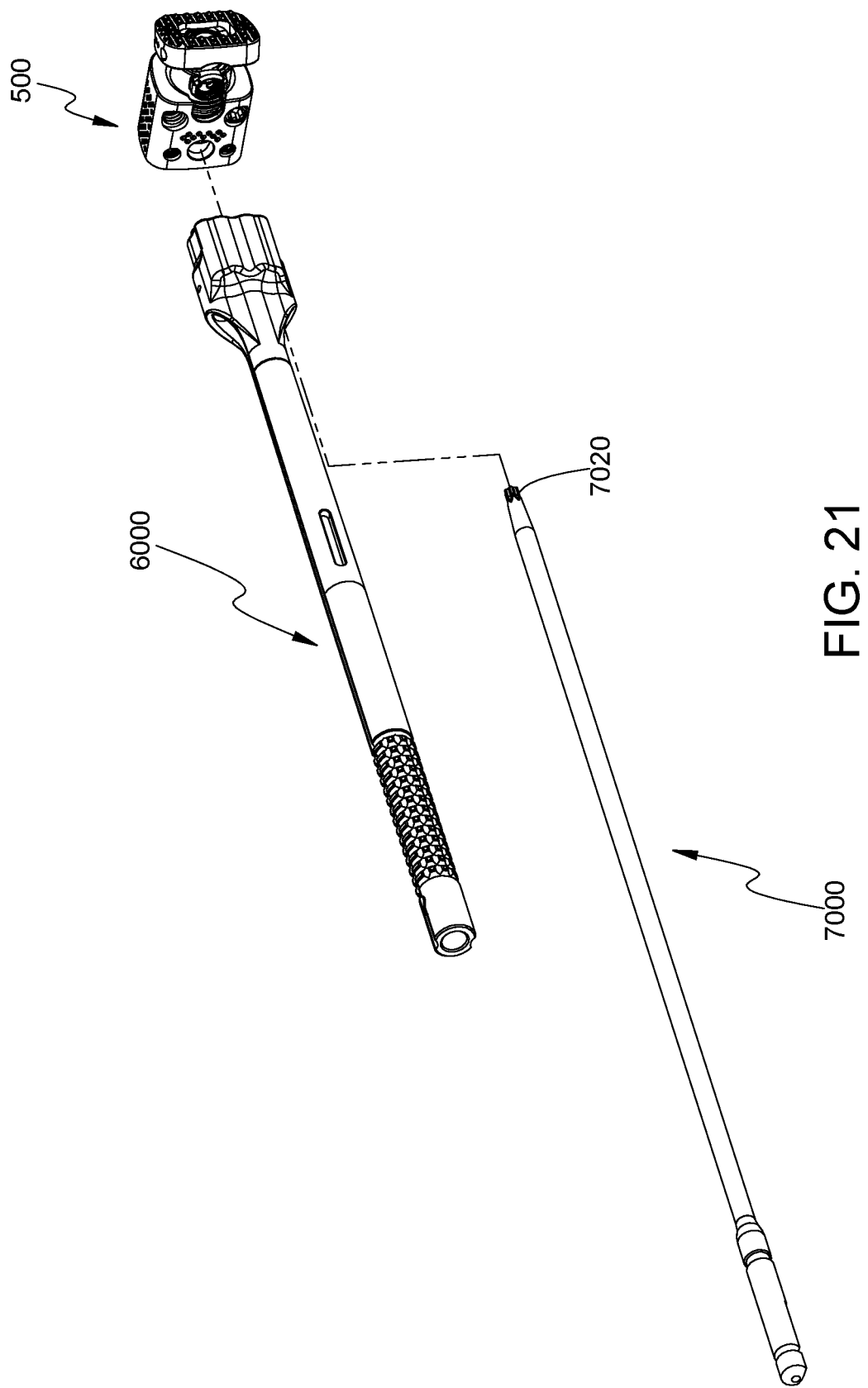
Figure 22:
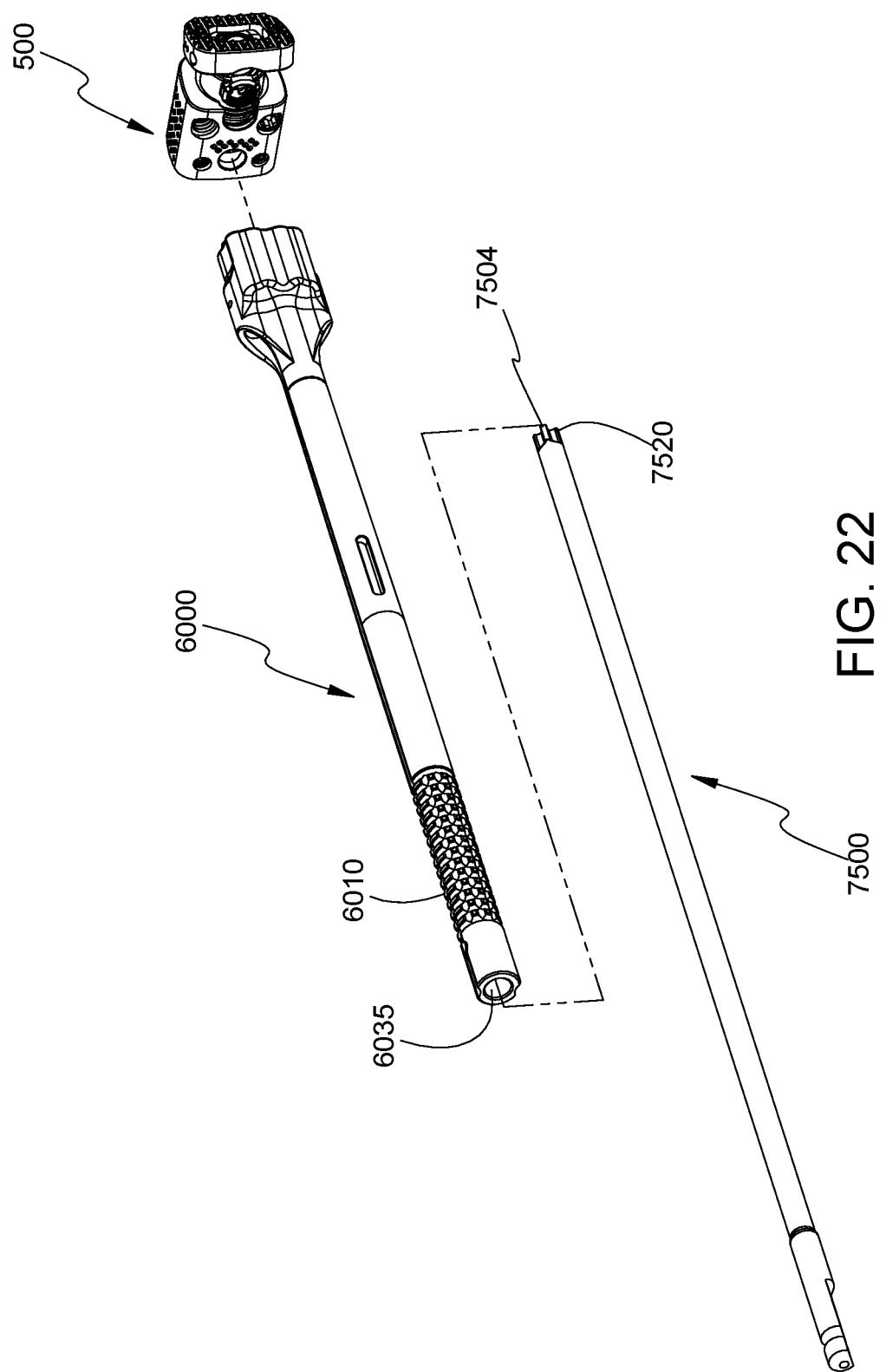
Figure 23:
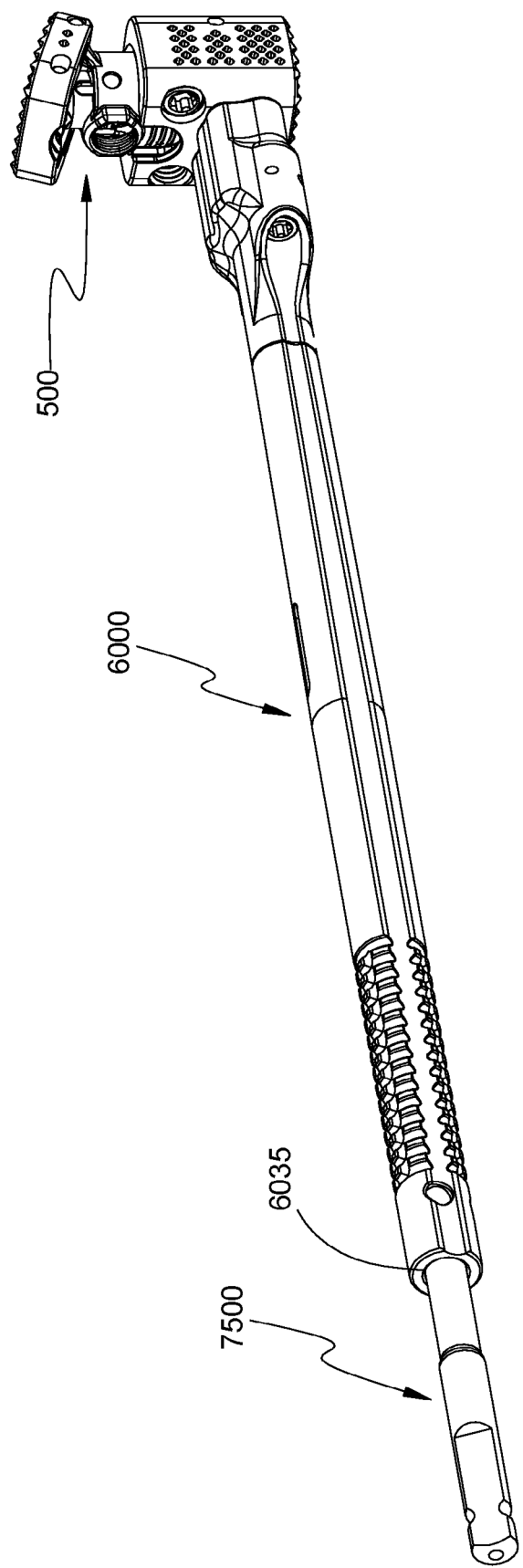

With reference to FIGS. 16 and 17, there is shown an insertion instrument 6000 for use with spinal fixation device 500 to position spinal fixation device 500 between adjacent vertebral bodies. Insertion instrument 6000 includes a handle 6010 and an elongate body 6020 extending from handle 6010. Insertion instrument 6000 defines a channel 6035 (FIG. 22) configured to receive an adjusting driver 7500 (FIG. 22). Elongate body 6020 includes engaging portion 6032 defining bores 6037 dimensioned to be aligned with bores 527a, 527c (FIG. 2) of housing 510. Bores 6037 of engaging portion 6032 are dimensioned to receive respective securing members 6039a, 6039b to secure insertion instrument 6000 with housing 510. Securing members 6039a, 6039b may be threadably coupled with respective bores 527a, 527c of housing 510 to securely attach spinal fixation device 500 with insertion instrument 6000 (FIG. 19).

With reference to FIGS. 18-23, when engaging portion 6032 of insertion instrument 6000 is secured with housing 510, respective securing members 6039a, 6039b (FIG. 17) are received within bores 527a, 527c of housing 510, respectively. A driver 7000 may be utilized to threadably secure securing members 6039a, 6039b within respective bores 527a, 527b. Alignment of securing members 6039a, 6039b with bores 527a, 527c provides alignment between bore 527b of housing 510 and channel 6035 of insertion instrument 6000. Adjusting driver 7500 may be inserted into channel 6035 of insertion instrument 6000 to engage teeth 612a (FIG. 2) of first rotatable member 610 with an engaging portion 7520 of the adjusting driver 7500. Rotation of adjusting driver 7500 rotates first rotatable member 610, causes axial displacement of first support 602, which, in turn, causes axial displacement of first end plate 540 with respect to housing 510. In this manner, end plate assembly 560 is selectively positionable relative to housing 510 through rotation of first rotatable member 610. In this manner, a length of spinal fixation device 500 may be selectively tailored to, e.g., the intervertebral space.

Figure 24:
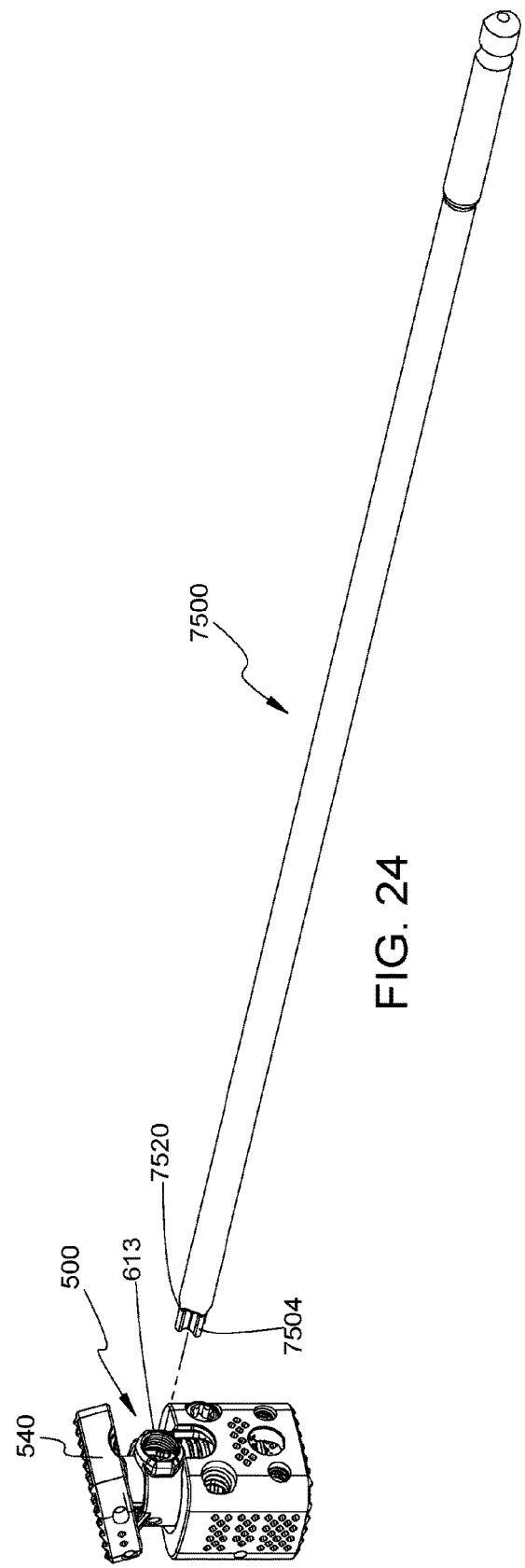
FIGS. 24 and 25 are perspective views of the adjusting driver of FIGS. 20-23 illustrating use with the spinal fixation device of FIG. 1.
Figure 25:
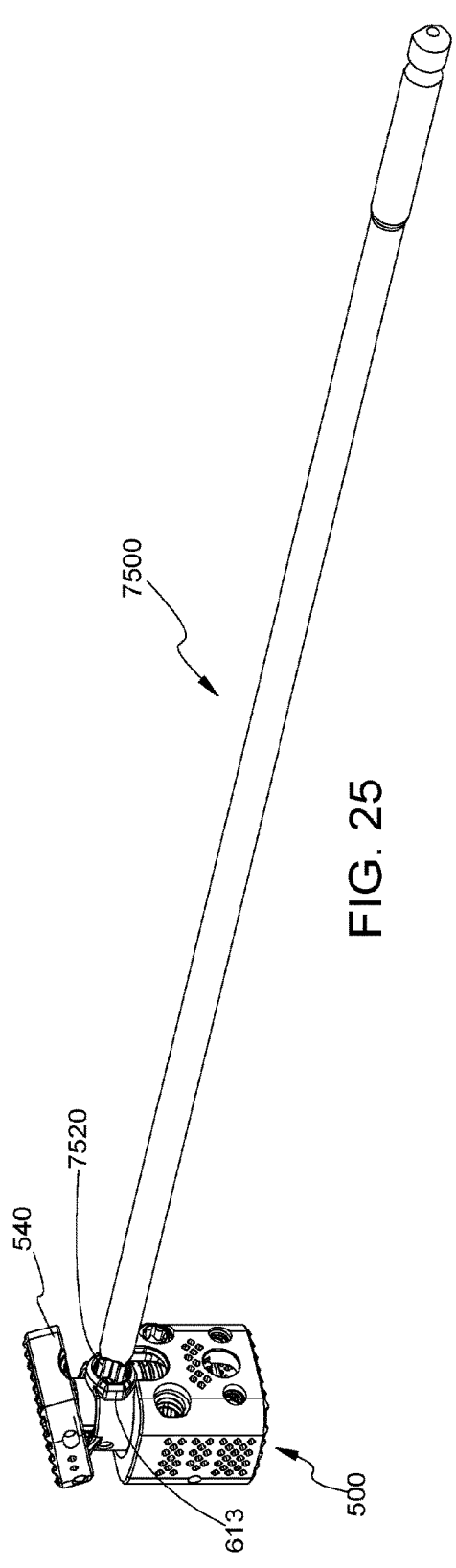
Figure 26:
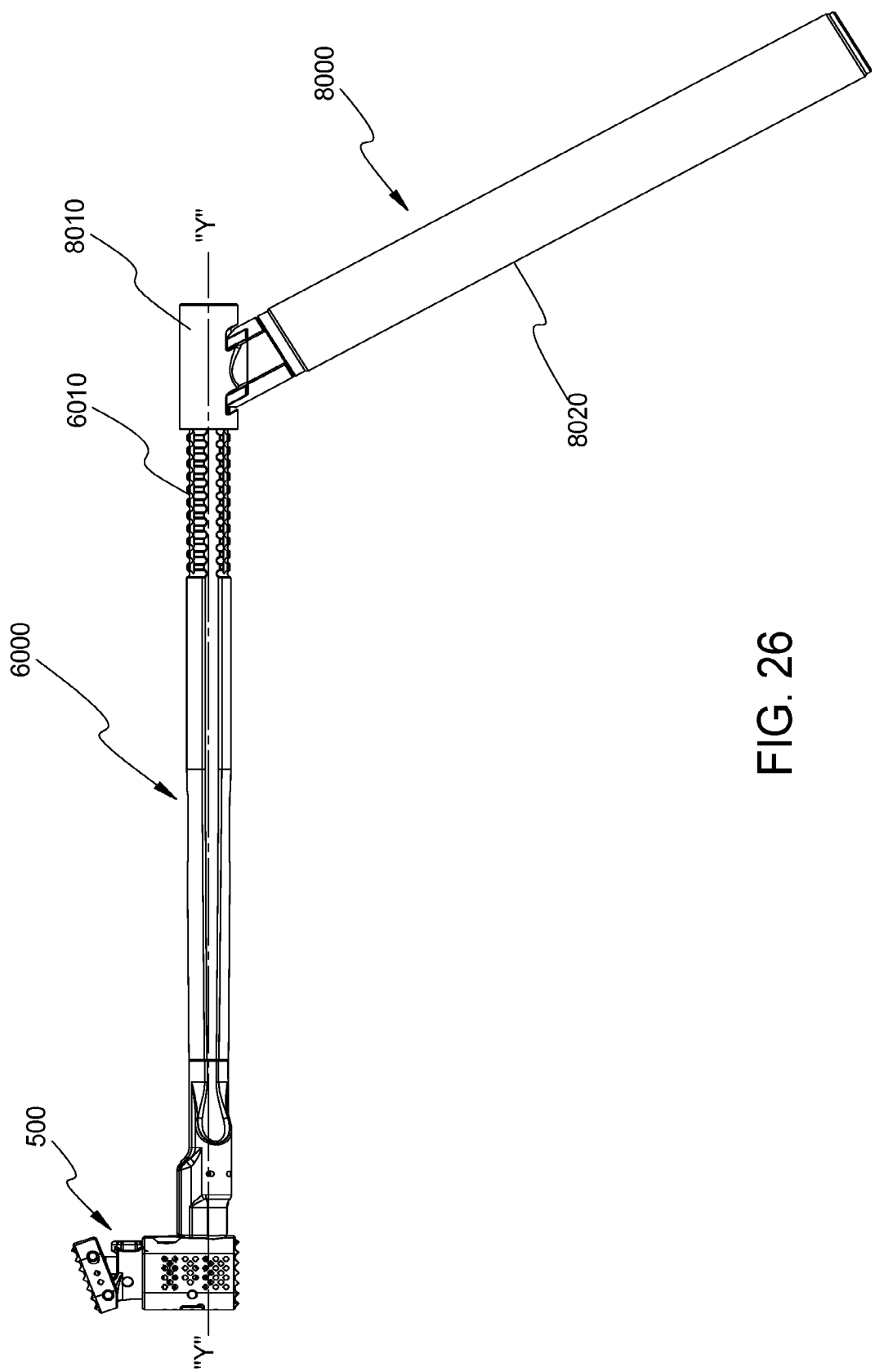
FIG. 26 is a side view of the insertion instrument of FIG. 16 and an extension member illustrating use with the spinal fixation device of FIG. 1.
Figure 27:
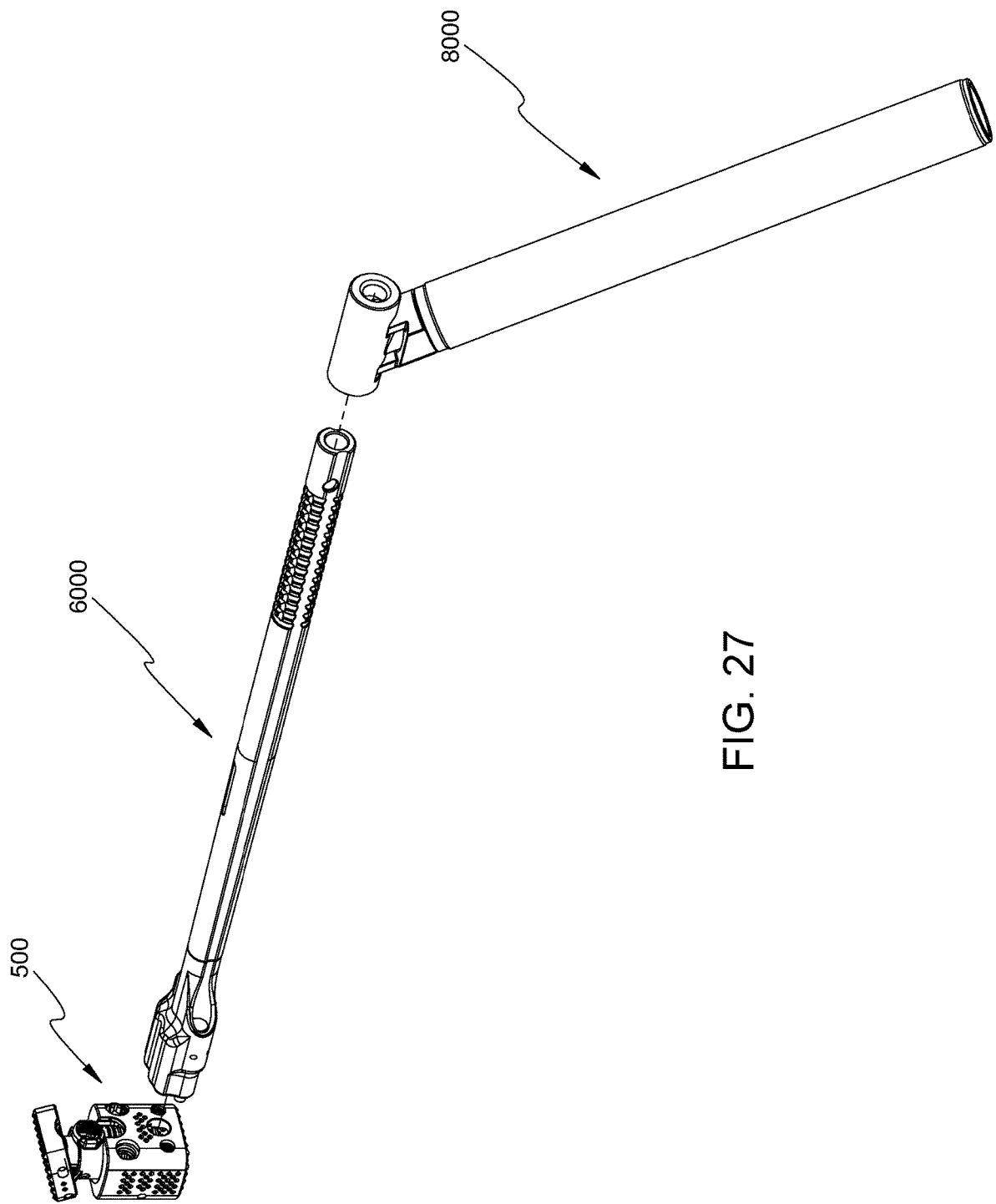
FIG. 27 is a perspective view of the insertion instrument of FIG. 16 and the extension member of FIG. 26 illustrating use with the spinal fixation device of FIG. 1.
Figure 29:
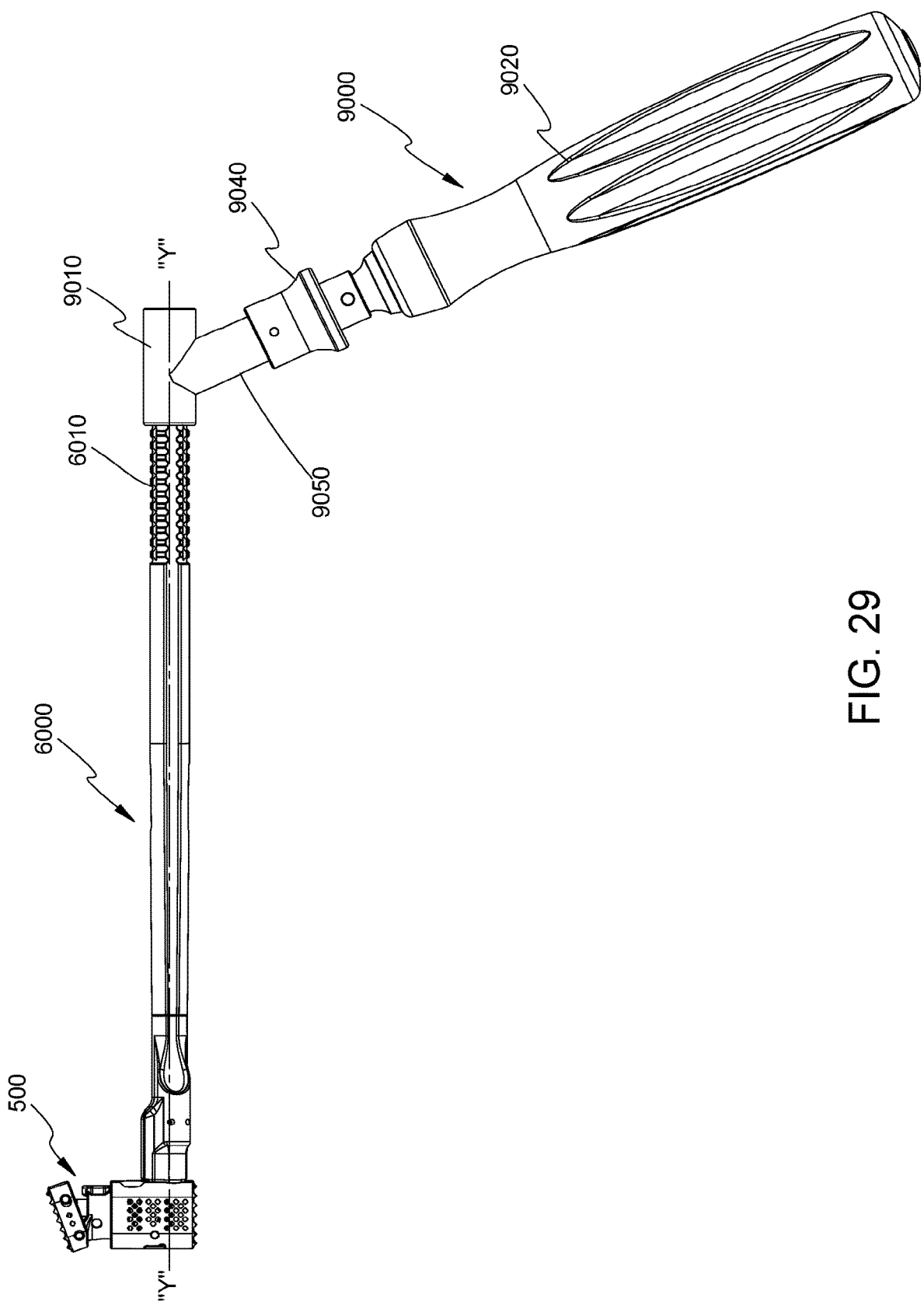
FIG. 29 is a side view of the insertion instrument of FIG. 26 and an extension member in accordance with another embodiment of the present disclosure illustrating use with the spinal fixation device of FIG. 1.
Figure 30:
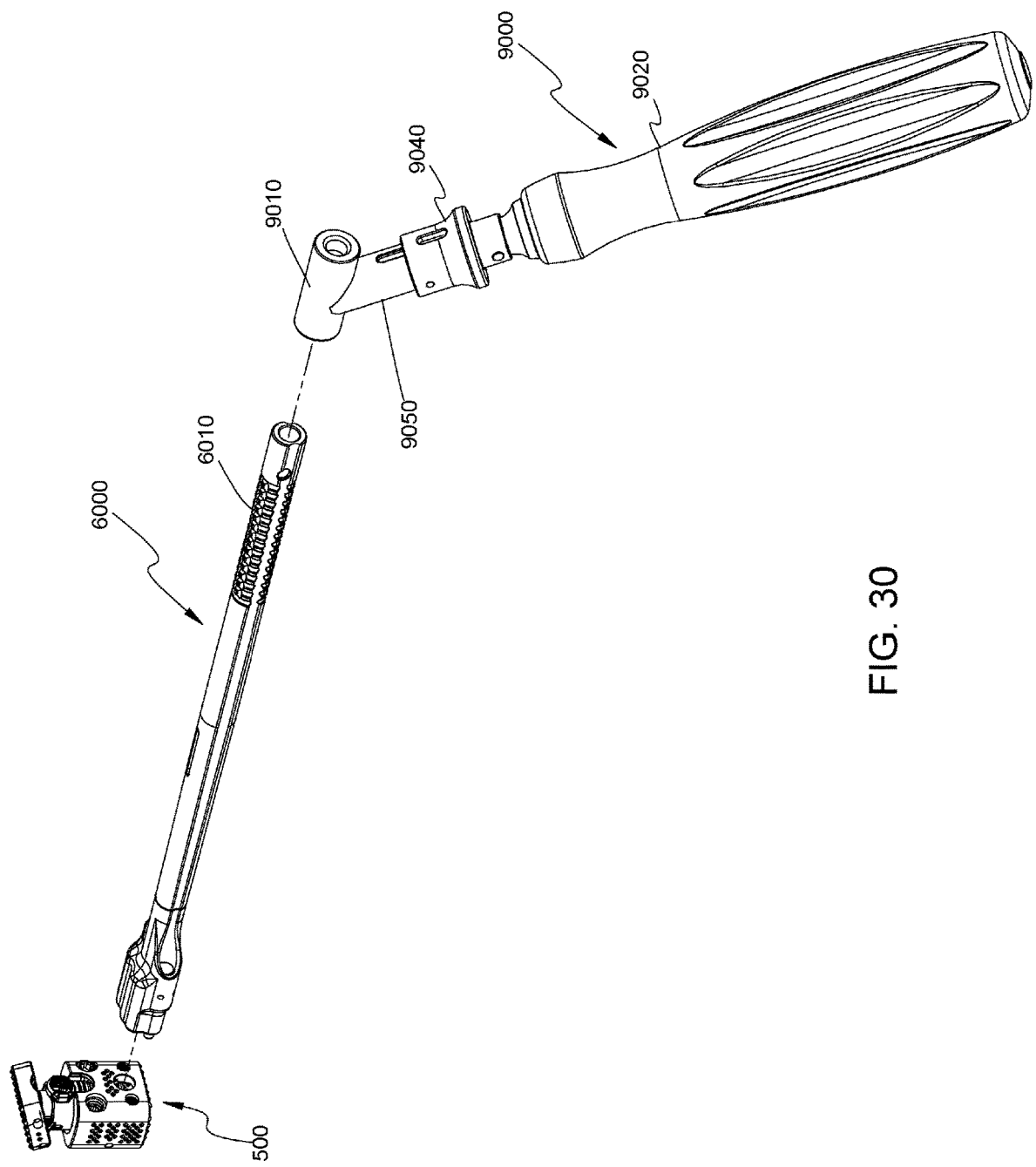
FIG. 30 is a perspective view of the insertion instrument and the extension member of FIG. 29 illustrating use with the spinal fixation device of FIG. 1.
Figure 31:
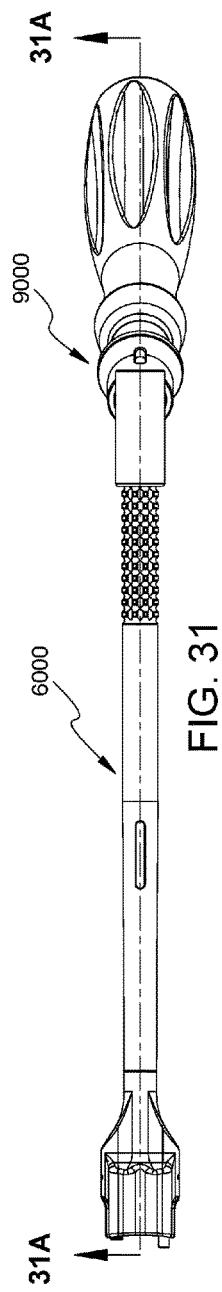
FIG. 31 is a top view of the insertion instrument and the extension member of FIG. 30.
Figure 31A:
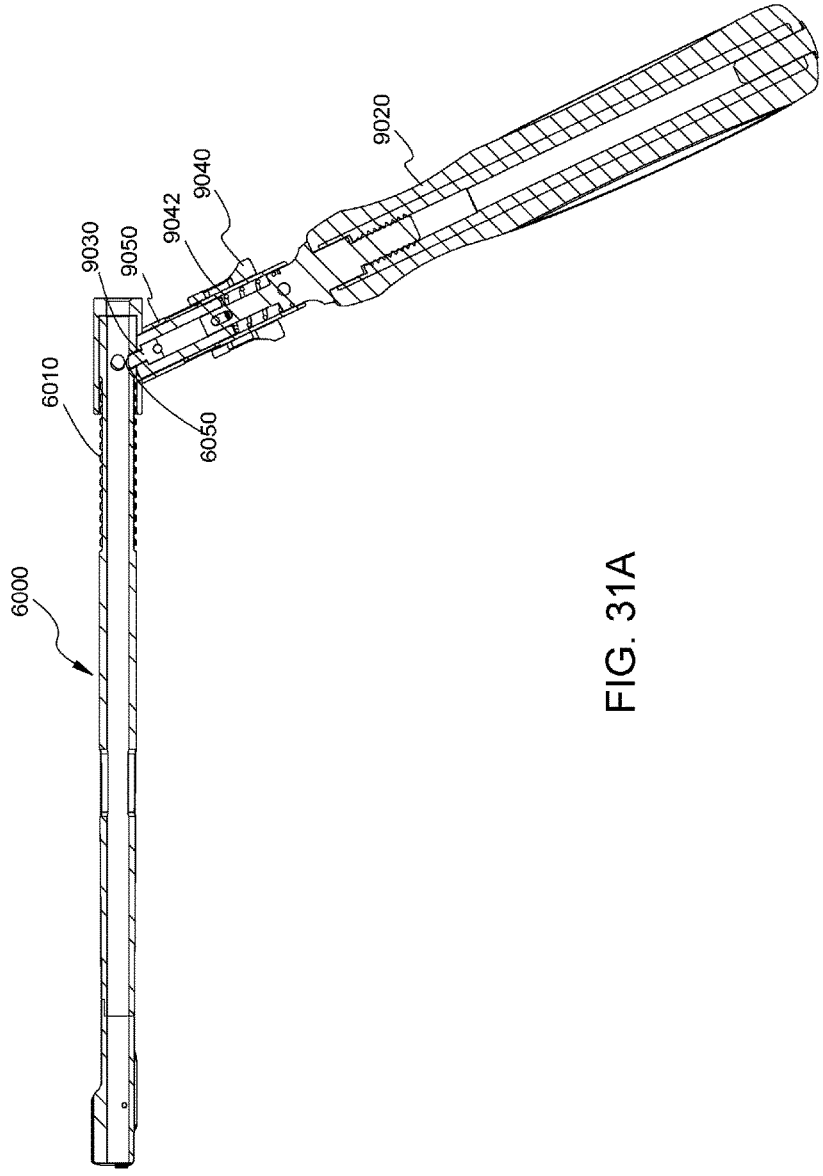
FIG. 31A is a cross-sectional view of the insertion instrument and the extension member of FIG. 31 taken along section line 31A-31A of FIG. 31.

With reference now to FIGS. 24 and 25, an engaging portion 7520 of adjusting driver 7500 may be inserted into locking bore 613 of first support 602 to operatively engage teeth 691 (FIG. 7) of second rotatable member 690. In this manner, when adjusting driver 7500 is rotated, teeth 691 of second rotatable member 690 rotatably engage engaging portion 7520 of adjusting driver 7500, which, in turn, causes axial displacement of second support 682 (FIG. 8) with respect to first support 602. This interaction causes angular displacement of first end plate 540 or pivoting of first end plate 540 about bore 604a (FIG. 7) of first support 602. Such a configuration enables the clinician to selectively adjust angular orientation of first end plate 540 with respect to housing 510 to achieve the desired lordosis.

Figure 10:
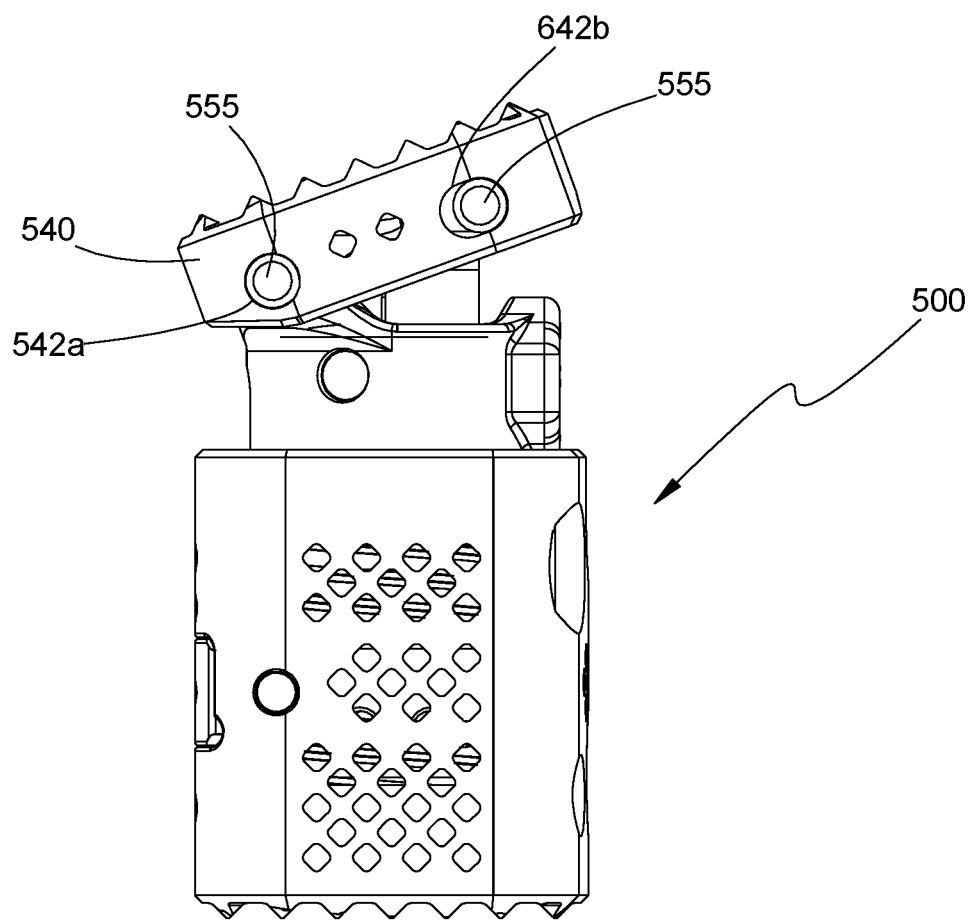
FIG. 10 is a side view of the spinal fixation device of FIG. 9 illustrating angular displacement of the first end plate.

In this manner, first end plate 540 may be advantageously angled to provide a desired amount of lordosis tailored to the need of each patient. For example, first end plate 540 may be positioned substantially orthogonal to the longitudinal axis "A-A" (FIG. 9) and adjacent first end 524 of housing 510. Alternatively, first end plate 540 may define an acute angle with respect to longitudinal axis "A-A" (FIG. 10) and spaced apart from first end 524 of housing 510.

With reference now to FIGS. 26-28A, insertion instrument 6000 may be provided with an extension member 8000 configured to be attached to insertion instrument 6000 to provide a handle offset from a longitudinal axis "Y" defined by insertion instrument 6000 to facilitate insertion of spinal fixation device 500 into the patient. In particular, extension member 8000 includes an engaging portion 8010 configured to, e.g., frictionally, receive handle 6010 of insertion instrument 6000, and a handle portion 8020. Handle portion 8020 extends from engaging portion 8010 such that handle portion 8020 is offset from longitudinal axis "Y-Y" of insertion instrument 6000.

With reference to FIGS. 29-31A, insertion instrument 6000 may be provided with an extension member 9000 in accordance with another embodiment of the present disclosure. Extension member 9000 includes an engaging portion 9010 configured to receive handle 6010 of insertion instrument 6000. Extension member 9000 further includes a handle portion 9020 extending from engaging portion 9010 such that handle portion 9020 is offset from longitudinal axis "Y-Y" of insertion instrument 6000. Handle portion 9020 includes a slider 9030 (FIG. 32) configured to engage notch 6050 defined in handle 6010 to further secure engaging portion 9010 with handle 6010. Slider 9030 is operatively coupled to collar 9040 disposed about a neck portion 9050 of handle portion 9020 such that sliding of collar 9040 transitions slider 9030 between an engaged position in which slider 9030 securely engages notch 6050 of handle 6010 and a disengaged position in which the slider 9030 is disengaged from notch 6050 of handle 6010. Collar 9040 may be coupled to a biasing member 9042 to bias slider 9030 towards the engaged state.

In use, the clinician first distracts vertebral bodies of interest to establish the intervertebral space. The clinician may then remove vertebral tissue, if necessary or desired. First and second supports 602, 682 of first support assembly 660 and second support assembly 680, respectively, are selectively positioned to achieve a desired orientation of first end plate 540 and length of spinal fixation device 500. Insertion instrument 6000 is coupled with spinal fixation device 500 by, e.g., threadably, coupling engaging portion 6032 (FIG. 17) with bores 527a, 527c (FIG. 2) of housing 510. Spinal fixation device 500 is then positioned adjacent a desired intervertebral space between vertebral bodies.

Upon inserting spinal fixation device 500 in the intervertebral space, adjusting driver 7500 can be inserted through channel 6035 (FIGS. 22 and 23) of insertion instrument 6000 to further adjust the axial distance between first end plate 540 and housing 510 by placing engaging portion 7520 through bore 527b defined in housing 510 such that teeth 7504 of engaging portion 7520 of adjusting driver 7500 engage teeth 612a of first rotatable member 610. In this manner, rotation of adjusting driver 7500 causes rotation of first rotatable member 610, which, in turn, imparts axial translation of first support 602. In this manner, the clinician may adjust the axial distance between first end plate 540 and housing 510, i.e., length of spinal fixation device 500. Adjusting driver 7500 is rotated until a desired length of spinal fixation device 500 is effected through axial movement of end plate assembly 560. At this time, screws 190 may be inserted into respective bores 521, 527b to secure the axial position of first support 602.

In addition, after removing adjusting driver 7500 and insertion instrument 6000, adjusting driver 7500 can be inserted into locking bore 613 (FIG. 4) of first support 602 to operatively engage teeth 691 (FIG. 4) of second rotatable member 690 (FIG. 7) to adjust the angular orientation of first end plate 540 with respect to housing 510 (i.e., axis "A-A") to mimic or closely match the degree of curvature along the spine comprising the adjacent vertebra. With reference to FIGS. 24 and 25, engaging portion 7520 of adjusting driver 7500 is inserted into locking bore 613 of first support 602 such that teeth 7504 of engaging portion 7520 of adjusting driver 7500 engage teeth 691 of second rotatable member 690. Rotation of adjusting driver 7500 causes rotation of second rotatable member 690, which, in turn, causes axial displacement of second support 682. Axial displacement of second support 682 with respect to first support 602 enables the clinician to adjust the angular orientation of first end plate 540 with respect to housing 510 to achieve the desired lordosis or kyphosis. It is contemplated that the clinician may make further adjustments by alternating length adjustment and angular adjustment to achieve the desired length of spinal fixation device 500 and angular orientation of first end plate 540. Upon achieving the desired length of spinal fixation device 500 and angular orientation of first end plate 540, screw 615 may be placed in locking bore 613. Screw 615 may be threadably secured in locking bore 613 by using driver 7000. In particular, screw 615 may include a boss 615a (FIG. 8) configured to be disposed between two adjacent teeth 691 of second rotatable member 690 to inhibit rotation of second rotatable member 690.

Although the illustrative embodiments of the present disclosure have been described herein with reference to the accompanying drawings, the above description, disclosure, and figures should not be construed as limiting, but merely as exemplifications of particular embodiments. For example, while the angular orientation of first end plate 540 is shown to be adjustable in cephalad and caudad directions, it is also contemplated that first end plate 540 may be adjustable in the medial and lateral directions. It is to be understood, therefore, that the disclosure is not limited to those precise embodiments, and that various other changes and modifications may be effected therein by one skilled in the art without departing from the scope or spirit of the disclosure.

What is claimed is:

1. A spinal fixation device comprising:
   a housing having a longitudinal axis;
   a first support assembly movable along the longitudinal axis;
   a second support assembly concentrically associated with the first support assembly; and
   an end plate rotatably coupled to the second support assembly; wherein:
   the first support assembly includes a first support and a first member rotatably secured in a chamber of the housing, the first support rotatably coupled to the first member such that rotation of the first member causes axial displacement of the first support; and
   the first support includes a protrusion portion pivotably coupled with a first end plate.

2. The spinal fixation device according to claim 1, wherein the first support defines a slot along the longitudinal axis, the housing including a pin configured to be received in the slot of the first support to facilitate axial movement of the first support.

3. The spinal fixation device according to claim 1, wherein the housing defines a first bore adjacent the first member.

4. The spinal fixation device according to claim 1, further comprising a first insert received within the first bore, the first insert configured to inhibit movement of the first support assembly.

5. The spinal fixation device according to claim 1, wherein the housing includes an inner wall having a ledge to inhibit axial displacement of the first member.

6. The spinal fixation device according to claim 1, wherein the first member includes circumferentially arranged teeth.

7. The spinal fixation device according to claim 1, wherein the second support assembly is movable from a first state in which the end plate defines a first angular orientation to a second state in which the end plate defines a second angular orientation.

8. The spinal fixation device according to claim 1, wherein the first support assembly is movable between a first position in which the end plate is spaced apart from the housing and a second position in which the end plate is adjacent the housing along the longitudinal axis.

9. The spinal fixation device according to claim 1, wherein at least a portion of the second support assembly is received within a passage of the first support assembly.

10. The spinal fixation device according to claim 1, wherein the protrusion portion of the first support defines a bore configured to receive a pin, the first end plate defining a slot configured to receive the pin such that axial displacement of the first support enables selective transition between a first position in which the end plate is a first distance from the housing and a second position in which the end plate is a second distance from the housing.

11. A spinal fixation device comprising:
    a housing having a longitudinal axis;
    a first support assembly movable along the longitudinal axis;
    a second support assembly concentrically associated with the first support assembly; and
    an end plate rotatably coupled to the second support assembly; wherein:
    the first support assembly includes a first support and a first member rotatably secured in a chamber of the housing, the first support rotatably coupled to the first member such that rotation of the first member causes axial displacement of the first support; and
    the second support assembly includes a second support and a second member rotatably secured in a passage of the chamber, the second support rotatably coupled to the second member such that rotation of the second member causes axial displacement of the second support.

12. The spinal fixation device according to claim 11, wherein the second support includes a protrusion portion operatively coupled with the first end plate.

13. The spinal fixation device according to claim 12, wherein the protrusion portion of the second support defines a bore configured to receive a pin, the first end plate defining a slot configured to receive the pin such that axial displacement of the second support enables selective transition of the first end plate from the first angular orientation to the second angular orientation.

14. The spinal fixation device according to claim 11, wherein the first support defines a second bore adjacent the second member.

15. The spinal fixation device according to claim 11, further comprising a second insert received within a second bore, the second insert configured to inhibit rotation of the second support assembly.

16. The spinal fixation device according to claim 11, wherein the second member includes circumferentially arranged teeth.

17. The spinal fixation device according to claim 11, wherein the second support assembly includes a second spacer having a bore and the second support defines a slot, the bore of the second spacer being aligned with the slot of the second support when the second support is received within the second spacer.

18. A spinal fixation device comprising:
a housing having a longitudinal axis;
a first support assembly movable along the longitudinal axis;
a second support assembly concentrically associated with the first support assembly; and
an end plate rotatably coupled to the second support assembly;
wherein the first support assembly includes a first spacer, and the housing including a first bore and a slot, the slot configured to receive the first spacer, the first spacer having a second bore configured to align with the first bore when the spacer is received within the slot.

19. The spinal fixation device according to claim 18, wherein the second support assembly is movable from a first state in which the end plate defines a first angular orientation to a second state in which the end plate defines a second angular orientation.

20. The spinal fixation device according to claim 18, wherein the first support assembly is movable between a first position in which the end plate is spaced apart from the housing and a second position in which the end plate is adjacent the housing along the longitudinal axis.

21. The spinal fixation device according to claim 18, wherein at least a portion of the second support assembly is received within a passage of the first support assembly.

* * * * *